US011485785B2

(12) United States Patent
Jakobovits et al.

(10) Patent No.: US 11,485,785 B2
(45) Date of Patent: Nov. 1, 2022

(54) ANTIBODIES CAPABLE OF BINDING HLA-A2/TYRD IN AN HLA RESTRICTED MANNER AND USES THEREOF

(71) Applicant: ADICET BIO, INC., Menlo Park, CA (US)

(72) Inventors: Aya Jakobovits, Beverly Hills, CA (US); Orit Foord, Foster City, CA (US); Daulet Kadyl Satpayev, Redwood City, CA (US); Mira Peled Kamar, Herzlia (IL); Galit Denkberg, Nofit (IL); Yoram Reiter, Haifa (IL); Ilan Beer, Haifa (IL); Keren Sinik, amat-Yishai (IL); Yael Teboul (Elbaz), Haifa (IL); Yael Shperber (Sery), Kfar-Vradim (IL); Reut Erel Segal, Haifa (IL); Ravit Oren, Haifa (IL); Dror Shmuel Alishekevitz, Kiryat-Tivon (IL)

( * ) Notice: Subject to any disclaimer, the term of this patent is extended or adjusted under 35 U.S.C. 154(b) by 301 days.

(21) Appl. No.: 16/622,892

(22) PCT Filed: Jun. 14, 2017

(86) PCT No.: PCT/IB2017/053539
§ 371 (c)(1),
(2) Date: Dec. 13, 2019

(87) PCT Pub. No.: WO2018/229530
PCT Pub. Date: Dec. 20, 2018

(65) Prior Publication Data
US 2020/0207858 A1 Jul. 2, 2020

(51) Int. Cl.
*C07K 16/28* (2006.01)
*A61P 35/00* (2006.01)
*A61K 39/00* (2006.01)

(52) U.S. Cl.
CPC .......... *C07K 16/2833* (2013.01); *A61P 35/00* (2018.01); *C07K 16/2809* (2013.01); *A61K 39/001102* (2018.08); *A61K 2039/505* (2013.01); *C07K 2317/24* (2013.01); *C07K 2317/31* (2013.01); *C07K 2317/565* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 2006/0159695 | A1 | 7/2006 | Delvecchio et al. |
| 2011/0105724 | A1 | 5/2011 | Clegg et al. |
| 2014/0294841 | A1 | 10/2014 | Scheinberg et al. |
| 2018/0171024 | A1 | 6/2018 | Peled Kamar et al. |
| 2018/0179283 | A1 | 6/2018 | Peled Farrar et al. |

FOREIGN PATENT DOCUMENTS

| EP | 2936158 | 2/2019 |
| WO | WO 03/068201 | 8/2003 |
| WO | WO 2007/143104 | 12/2007 |
| WO | WO 2008/120202 | 10/2008 |
| WO | WO 2011/062560 | 5/2011 |
| WO | WO 2012/091563 | 7/2012 |
| WO | WO 2012/109659 | 8/2012 |
| WO | WO 2012/135854 | 10/2012 |
| WO | WO 2013/105856 | 7/2013 |
| WO | WO 2014/011489 | 1/2014 |
| WO | WO 2015/070078 | 5/2015 |
| WO | WO 2016/161390 | 10/2016 |
| WO | WO 2016/199140 | 12/2016 |
| WO | WO 2016/199141 | 12/2016 |
| WO | WO 2018/229530 | 12/2018 |

OTHER PUBLICATIONS

U.S. Appl. No. 15/579,974, entitled, "T Cell Receptor Like Antibodies Having Fine Specificity", filed Dec. 6, 2017, of Adicet Bio, Inc. (Published as 2018-0179283 on Jun. 28, 2018).
U.S. Appl. No. 15/579,616, entitled, "Affinity Entities Comprising a Tcr-Like Antibody Binding Domain With High Affinity and Fine Specificity and Uses of Same", filed Dec. 5, 2017, of Adicet Bio, Inc. (U.S. Pat. No. 11,001,642 issued on May 11, 2021).
U.S. Appl. No. 17/317,824, entitled, "Affinity Entities Comprising a Tcr-Like Antibody Binding Domain With High Affinity and Fine Specificity and Uses of Same", filed May 11, 2021, of Adicet Bio, Inc. (Published as 2021-0388111 on Dec. 16, 2021).
Almargo and Fransson,"Humanization of antibodies", Frontiers in Bioscience, vol. 13, pp. 1619-1633 (2008).
Cameron et al. "identification of A Titin-Derived HLA-AI-Presented Peptide as A Cross-Reactive Target for Engineered MAGE A3-Directed T Cells", Science Translational Medicine, 5(197): 197ra103-1-197ra103-11, Aug. 7, 2013.
Cameron et al. Supplementary Materials for "Identification of A Titin-Derived HLA-AI-Presented Peptide as A Cross-Reactive Target for Engineered MAGE A3-Directed T Cells", Science Translational Medicine, 5(197): 197ra103-1-197ra103-11, Aug. 7, 2013.
Cohen et al. "T-Cell Receptor-Like Antibodies: Targeting the Intracellular Proteome Therapeutic Potential and Clinical Applications", Antibodies, 2: 517-534, 2013.
Dao et al. "Targeting the Intracellular WT1 Oncogene Product With A Therapeutic Human Antibody", Science Translational Medicine, 5(176): 176ra33-1-176ra33-11, Mar. 13, 2013.
De Genst et al., "Antibody repertoire development in camelids", Dev Comp Immunol, vol. 30, pp. 187-198 (2006).

(Continued)

*Primary Examiner* — Nelson B Moseley, II
(74) *Attorney, Agent, or Firm* — Todd Lorenz

(57) ABSTRACT

Antibodies capable of binding HLA-A2/Tyrosinase (TyrD) in an HLA restricted manner are provided. Specifically, the antibodies are capable of binding HLA-A2/TyrD369-377 in an HLA restricted manner. Further provided are complementary determining region (CDR) sequences of heavy chain and light chain of antibodies, and methods of using the antibodies for the treatment of cancer.

39 Claims, 8 Drawing Sheets

Specification includes a Sequence Listing.

(56) References Cited

OTHER PUBLICATIONS

Dhanik et al. "In-Silico Discovery of Cancer-Specific Peptide-HLA Complexes For Targeted Therapy", BMC Bioinformatics, 17(1): 286 pp. 1-19, Jul. 2016.
Greenberg "Function of T Cells and Their Therapeutic Application in Cancer", Annual Meeting of the American Association for Cancer Research, AACR, New Orleans, LA, USA, Apr. 16-20, 2016, Poster Presentation, Apr. 2016.
Hillig et al. "High-Resolution Structure of HLA-A*0201 in Complex With A Tumour-Specific Antigenic Peptide Encoded by the MAGE-A4 Gene", Journal of Molecular Biology, JMB, XP004466111, 310(5): 1167-1176, Jul. 27, 2001. p. 1173, 1-h col., Figs.1-5.
Huehls et al, "Bispecific T-cell engagers for cancer immunotherapy", Immunology and Cell Biology, AU, vol. 93, No. 3, pp. 290-296 (2014).
Jaigirdar et al. "A High-Avidity WT-1-Reactive T-Cell Receptor Mediates Recognition of Peptide and Processed Antigen But Not Naturally Occurring WT-1-Positive Tumor Cells", Journal of Immunotherapy, 39(3): 105-116, Apr. 2016. Abstract.
Jones Tim D et al, "Deimmunization of Monoclonal Antibodies", Antibody-Drug Conjugates; In: Methods in Molecular Biology; ISSN 1064-3745; vol. 263; Methods in Molecular Biology, vol. 525, pp. 405-423 (2009).
Khee Hwang W Y et al, "Use of human germline genes in a CDR homology-based approach to antibody humanization", Methods, Academic Press, NL, vol. 36, No. 1, pp. 35-42, (2005).
Lev et al. "Isolation and Characterization of Human Recombinant Antibodies Endowed With the Antigen-Specific, Major Histocompatibility Complex-Restricted Specificity of T Cells Directed Toward the Widely Expressed Tumor T-Cell Specificity of T Cells Directed Toward the Widely Expressed Tumor T-Cell Epitopes of the Telomerase Catalytic Subunit", Cancer Research, XP007918401, 62(11): 3184-3194, Jun. 1, 2002. p. 3190, Figs.7, 8, Table 1.
Low et al. "Binding of TCR Multimers and a TCR-Like Antibody with Distinct Fine-Specificities is Dependent on the Surface Density of HLA Complexes", PloS one, 7(12): e51397 1-11, Dec. 10, 2012. Abstract. Fig. 3.
Mareeva et al. "How A T Cell Receptor-Like Antibody Recognizes Major Histocompatibility Complex-Bound Peptide", The Journal of Biological Chemistry, XP055226212, 283(43): 29053-29059, Published Online Aug. 14, 2008. p. 29056, r-h col.
Michaeli et al. "Expression Hierarchy of T Cell Epitopes From Melanoma Differentiation Antigens: Unexpected High Level Presentation of Tyrosinase-HLA-A2 Complexes Revealed b Peptide-Specific, MHC-Restricted, TCR-Like Antibodies", The Journal of Immunology, XP007918402,182(10): 6328-6341, May 15, 2009. Figs.1-9.
Michaeli et al. "Melanoma Cells Present High Levels of HLA-A2-Tyrosinase in Association With Instability and Aberrant Intracellular Processing of Tyrosinase", European Journal of Immunology, XP055225865, 42(4): 842-850, Apr. 1, 2012. p. 6329, 1-h col., Para 3-r-h col., Para 6, Figs.4, 7, 8.
Olson, et al., "HLA-A2-restricted T-cell epitopes specific for prostatic acid phosphatase," Cancer Immunol. Immunother., vol. 59(6), pp. 943-953 (2010).
Oehlrich et al. "Generation of RAGE-1 and MAGE-9 Peptide-Specific Cytotoxic T-Lymphocyte Lines for Transfer in Patients With Renal Cell Carcinoma", International Journal of Cancer, XP008126877, 117: 256-264, Published Online May 15, 2005. Table 1.
Scheinberg, et al., "A Cytootxic human monoclonal antibody recognizing cell surface wt1 peptide/HLA-A2 complex", Blood, vol. 118(21), pp. 1677 (2011).
Sim "The Development, Characterization and Application of the TCR-Like Monoclonal Antibodies With Specificity for Epstein-Barr Virus Latent Epitopes", Thesis for Degree of Doctor of Philosophy, National University of Singapore, XP055226231, 6 P., Jan. 1, 2012. p. 136, Lines 3-11, Rules 3011, Figs.4.2, 5.1.
Sim "The Development, Characterization and Application of the TCR-Like Monoclonal Antibodies With Specificity for Epstein-Barr Virus Latent Epitopes: Application of TCR-Like Monoclonal Antibodies", National University of Singapore, Thesis, XP055226234, Chap.5(Results III): 134137, Jan. 1, 2012.
Sim "The Development, Characterization and Application of the TCR-Like Monoclonal Antibodies With Specificity for Epstein-Barr Virus Latent Epitopes: Characterization of TCR-Like Monoclonal Antibodies HLA-A0201/EBNA-1, HLA-A0201/LMP1 and HLA-A0201/EMP2A", University of Singapore, Thesis, XP055226265, Chap.4(Results II): 122-133, Jan. 1, 2012.
Yoshinaga et al., "Ig L-chain shuffling for affinity maturation of phage library-derived human anti-human MCP-1 antibody blocking its chemotactic activity", J. Biochem, vol. 143, pp. 593-601 (2008).

Figure 1 hD11-5

Light Chain VK nucleic acids (SEQ ID NO: 1):

FR1-CDR1-FR2-CDR2-FR3-CDR3-FR4- Constant region-stop codon

GACATCCAGATGACCCAGTCTCCATCCTCCCTGTCTGCATCTGTAGGAGACAGAGTCACCATCACTTGCAAGGCGA
GTCAGGACATTCACAACTATATAGCTTGGTATCAGCAGAAACCAGGGAAAGCCCCTAAGCTCCTGATCCACTATAC
ATCCACTTTGCAACCAGGGGTCCCATCAAGGTTCAGTGGAAGTGGATCTGGGACAGATTTTACTTTCACCATCAGC
AGCCTGCAGCCTGAAGATATTGCAACATATTACTGTCTACAGTATGATAATCTCTGGACGTTCGGTCAAGGCACCA
AGGTGGAAATCAAACGGACCGTGGCCGCACCTAGTGTGTTCATCTTCCCTCCCTCCGACGAGCAGCTGAAGTCTG
GCACCGCCTCCGTGGTCTGCCTGCTGAACAACTTCTACCCTCGGGAGGCCAAGGTGCAGTGGAAGGTGGACAACG
CCCTGCAGTCCGGCAACTCCCAGGAATCCGTCACCGAGCAGGACTCCAAGGACTCTACCTACTCCCTGTCCTCCAC
CCTGACCCTGTCCAAGGCCGACTACGAGAAGCACAAGGTATACGCCTGCGAGGTCACCCACCAGGGCCTGTCCTC
TCCCGTCACCAAGTCCTTCAACCGGGGCGAGTGCTGA

Light Chain VK amino acids sequence (SEQ ID NO: 2):

DIQMTQSPSSLSASVGDRVTITCKASQDIHNYIAWYQQKPGKAPKLLIHYTSTLQPGVPSRFSGSGSGTDFTFTISSLQPE
DIATYYCLQYDNLWTFGQGTKVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Heavy Chain VH-5 nucleic acids (SEQ ID NO: 3):

FR1-CDR1-FR2-CDR2-FR3-CDR3-FR4- Constant region-stop codon

CAGATCACCTTGAAGGAGTCTGGTCCTACGCTGGTGAAACCCACACAGACCCTCACGCTGACCTGCACCTTCTCTG
GGTTCTCACTCAGCACTAGTGGAATGGGTGTGTCCTGGATCCGTCAGCCCCCAGGAAAGGCCCTGGAGTGGCTTG
CACACATTTATTGGGATGATGATAAGCGCTACAACCCATCTCTGAAGAGCAGGCTCACCATCACCAAGGACACCTC
CAAAAACCAGGTGGTCCTTACAATGACCAACATGGACCCTGTGGACACAGCCACATATTACTGTGCACGAAAGGA
CTACGGTAGTAGCTTCTATGCTATGCACTACTGGGGTCAAGGAACCCTAGTCACCGTCTCGAGTGCCTCTACCAAG
GGCCCTTCCGTGTTCCCTCTGGCCCCCAGCTCGAAGTCCACCTCCGGCGGCACCGCCGCTCTGGGCTGCCTGGTCA
AGGACTACTTCCCTGAGCCTGTGACAGTGTCCTGGAACTCTGGCGCTCTGACCTCTGGCGTGCATACCTTCCCTGCC
GTGCTGCAGTCCTCCGGCCTGTACTCCCTGTCCTCTGTGGTCACAGTGCCTTCCTCCTCCCTGGGCACCCAGACCTA
CATCTGCAACGTGAACCACAAGCCTTCCAACACCAAGGTGGACAAGAAGGTGGAGCCTAAGTCCTGCGACAAGAC
CCACACCTGTCCTCCCTGCCCTGCTCCTGAGCTGCTGGGCGGACCCTCCGTGTTCCTGTTCCCTCCTAAGCCTAAGG
ACACCCTGATGATCTCCCGGACCCCTGAGGTCACCTGTGTGGTGGTGGATGTGTCCCACGAGGATCCTGAGGTCA
AGTTCAATTGGTACGTGGACGGCGTGGAGGTGCACAACGCCAAGACAAAGCCACGCGAGGAACAGTACAACTCC
ACCTACCGGGTGGTGTCCGTGCTGACCGTGCTGCACCAGGACTGGCTGAACGGCAAAGAGTACAAGTGCAAGGT
CTCCAACAAGGCCCTGCCTGCCCCCATCGAGAAAACCATCTCCAAGGCCAAGGGACAGCCTCGCGAGCCTCAGGT
GTACACCCTGCCTCCCTCTCGGGATGAACTGACCAAGAATCAGGTGTCCCTGACATGTCTGGTCAAGGGCTTCTAC
CCTTCCGATATCGCCGTGGAGTGGGAGTCCAACGGCCAGCCTGAGAACAACTACAAGACCACCCCTCCTGTGCTG
GACTCCGACGGCTCTTTCTTCCTGTACTCCAAGCTGACCGTGGACAAGTCCCGGTGGCAGCAGGGCAACGTGTTCT
CCTGCTCCGTGATGCACGAGGCCCTGCACAACCACTACACCCAGAAGTCTCTGTCCCTCTCTCCCGGCTGA

Heavy Chain VH-5 amino acids sequence (SEQ ID NO: 4):

QITLKESGPTLVKPTQTLTLTCTFSGFSLSTSGMGVSWIRQPPGKALEWLAHIYWDDDKRYNPSLKSRLTITKDTSKNQV
VLTMTNMDPVDTATYYCARKDYGSSFYAMHYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPG

Figure 1 continued

A. HLA-A2+/Tyr+ Melanoma cell lines
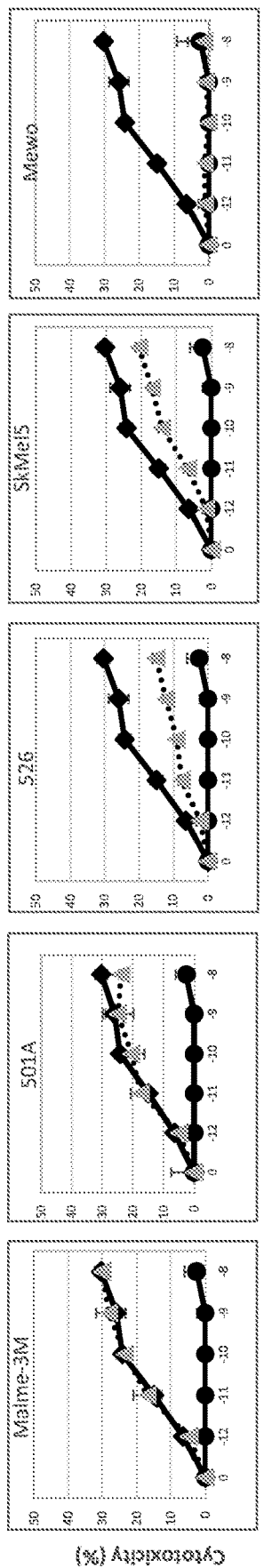
B. HLA-A2+/Tyr-
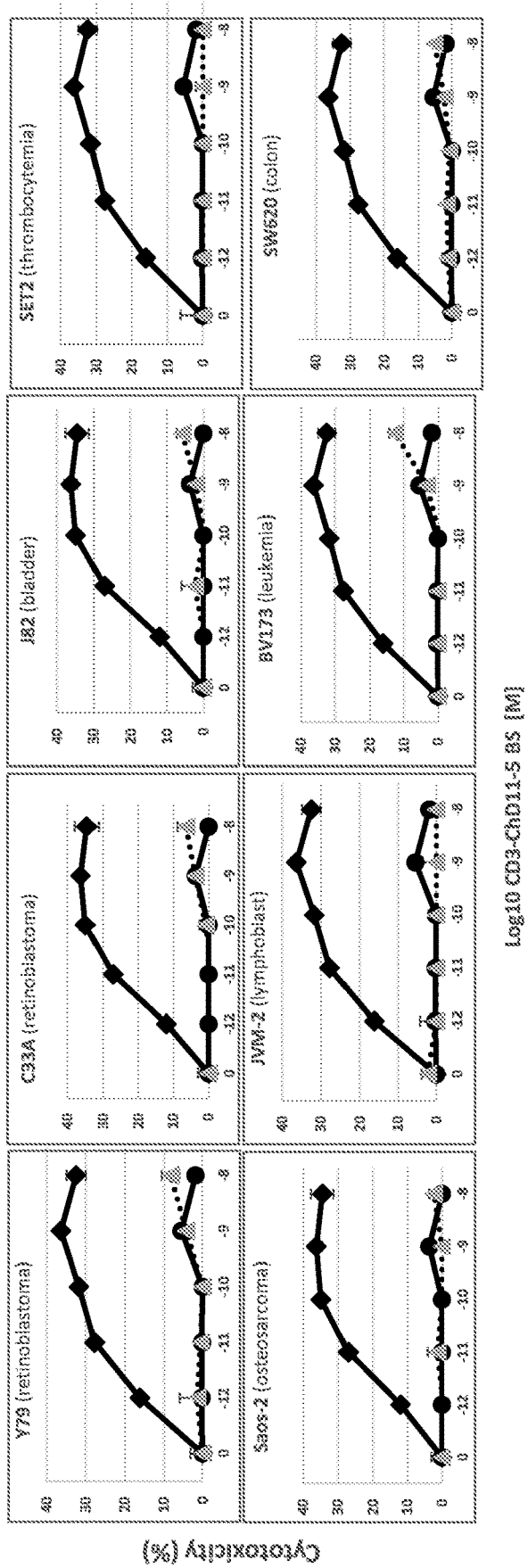
Figure 5

ANTIBODIES CAPABLE OF BINDING HLA-A2/TYRD IN AN HLA RESTRICTED MANNER AND USES THEREOF

FIELD AND BACKGROUND OF THE INVENTION

The present invention, in some embodiments thereof, relates to antibodies capable of binding HLA-A2/TyrD in an HLA restricted manner and uses thereof.

Tumor and virus-infected cells are recognised by CD8+ cytotoxic T cells that, in response, are activated to eliminate these cells. In order to be activated, the clonotypic T-cell receptor (TCR) needs to encounter a specific peptide antigen presented by the membrane surface major histocompatibility complex (MHC) molecule. Cells that have undergone malignant transformation or viral infection present peptides derived from tumour-associated antigens or viral proteins on their MHC class I molecules. Therefore, disease-specific MHC-peptide complexes are desirable targets for immunotherapeutic approaches. One such approach transforms the unique fine specificity but low intrinsic affinity of TCRs to MHC-peptide complexes into high-affinity soluble antibody molecules endowed with a TCR-like specificity towards tumour or viral epitopes. These antibodies, termed TCR-like antibodies, are being developed as a new class of immunotherapeutics that can target tumour and virus-infected cells and mediate their specific killing. In addition to their therapeutic capabilities, TCR-like antibodies are being developed as diagnostic reagents for cancer and infectious diseases, and serve as valuable research tools for studying MHC class I antigen presentation.

Melanomas are aggressive, frequently metastatic tumors derived from either melanocytes or melanocyte related nevus cells. Even when melanoma is apparently localized to the skin, up to 30% of patients develop systemic metastasis. Classic treatment modalities of melanoma include surgery, radiation and chemotherapy. In the past decade immunotherapy and gene therapy have emerged as new and promising methods for treating melanoma.

WO03/068201 discloses methods of producing TCR-like antibodies to tumor antigens including tyrosinase.

WO2008/120202 discloses TCR-like antibodies to HLA-Tyrosinase$_{369-377}$ complex.

Additional background art includes:

SUMMARY

According to an aspect of some embodiments of the present invention there is provided an antibody comprising an antigen binding domain comprising CDR sequences which are N—C ordered:

```
CDR1 Heavy
Chain (HC)
                                            SEQ ID NO: 8
TSGMGVS CDR2 HC
                                            SEQ ID NO: 9
HIYWDDDKRYNPSLKS

CDR3 HC
                                            SEQ ID NO: 10
KDYGSSFYAMHY

CDR1 Light
Chain (LC)
                                            SEQ ID NO: 5
KASQDIHNYIA

CDR2 LC
                                            SEQ ID NO: 6
YTSTLQP

CDR3 LC
                                            SEQ ID NO: 7
LQYDNLWT
``` wherein a variable region of the heavy chain of the antibody is as set forth in SEQ ID NO: 4 and the antibody is capable of binding HLA-A2/Tyr$_{D369-377}$ in an HLA restricted manner.

According to an aspect of some embodiments of the present invention there is provided an antibody comprising an antigen binding domain comprising CDR sequences which are N—C ordered:

```
CDR1 Heavy
Chain (HC)
                                            SEQ ID NO: 8
TSGMGVS CDR2 HC
                                            SEQ ID NO: 9
HIYWDDDKRYNPSLKS

CDR3 HC
                                            SEQ ID NO: 10
KDYGSSFYAMHY

CDR1 Light
Chain (LC)
                                            SEQ ID NO: 5
KASQDIHNYIA

CDR2 LC
                                            SEQ ID NO: 6
YTSTLQP

CDR3 LC
                                            SEQ ID NO: 7
LQYDNLWT
``` wherein a variable region of the heavy chain of the antibody is as set forth in SEQ ID NO: 4, a variable region of the light chain of the antibody is as set forth in SEQ ID NO: 2 and the antibody is capable of binding HLA-A2/Tyr$_{D369-377}$ in an HLA restricted manner.

According to some embodiments of the invention, the antibody is IgG.

According to some embodiments of the invention, the antibody is a chimeric antibody.

According to some embodiments of the invention, the antibody is an antibody fragment.

According to some embodiments of the invention, the antibody is selected from the group consisting of Fab, F(ab')2, Fv, scFv, dsFv and a single domain molecule.

According to some embodiments of the invention, the heavy chain of the antibody is as set forth in SEQ ID NO: 21 or 27.

According to some embodiments of the invention, the light chain of the antibody is as set forth in SEQ ID NO: 2, 19 or 25.

According to some embodiments of the invention, the antibody comprises a therapeutic moiety.

According to some embodiments of the invention, the therapeutic moiety is selected from the group consisting of a cytotoxic moiety, a toxic moiety, a cytokine moiety and a drug.

According to some embodiments of the invention, the therapeutic moiety comprises a cell.

According to some embodiments of the invention, the cell is selected from the group consisting of an αβ T-cell, γδ T-cell, NK, CIK, NKT, macrophage and a B cell.

According to some embodiments of the invention, the antibody is a bispecific antibody.

According to some embodiments of the invention, the bispecific antibody comprises an anti-CD3 or an anti-CD16.

According to some embodiments of the invention, the anti-CD3 comprises an scFv.

According to some embodiments of the invention, a light chain of the antibody capable of binding HLA-A2/Tyr$_{D369-377}$ in an HLA restricted manner is comprises SEQ ID NO: 2.

According to an aspect of some embodiments of the present invention there is provided an isolated polynucleotide comprising a nucleic acid sequence encoding the antibody.

According to an aspect of some embodiments of the present invention there is provided an expression vector comprising the polynucleotide operably linked to a cis-acting regulatory element.

According to some embodiments of the invention, the expression vector is a viral vector.

According to an aspect of some embodiments of the present invention there is provided a cell comprising the polynucleotide or the expression vector.

According to an aspect of some embodiments of the present invention there is provided a pharmaceutical composition comprising the antibody, the vector of claim or the cell.

According to an aspect of some embodiments of the present invention there is provided a method of treating melanoma or glioblastoma, comprising administering to a subject in need thereof a therapeutically effective amount of the antibody, the vector or the cell, thereby treating the melanoma or glioblastoma.

According to an aspect of some embodiments of the present invention there is provided, the antibody, the vector or the cell in the treatment of melanoma or glioblastoma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows that nucleotide and amino acid sequences of humanized D11 (hD11-5) TCRL antibody heavy and light chains (comprising SEQ ID NOs. 1-4 and 24-27).

FIGS. 5A-B show killing of HLA-A2+/Tyr+ and HLA-A2+/Tyr− cell lines by CD3-ChD11-5 bispecific (BS) TCRL (SEQ D NOs: 16-21).

DESCRIPTION OF SPECIFIC EMBODIMENTS OF THE INVENTION

The present invention, in some embodiments thereof, relates to antibodies capable of binding HLA-A2/TyrD in an HLA restricted manner and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

T Cell Receptor (TCR)-like (TCRL) antibodies are endowed with a TCR-like specificity toward tumor epitopes. Unlike TCRs which exhibit low affinity to the HLA-peptide antigen complex, TCRLs are characterized by affinity even at their soluble form. TCRLs are being developed as a new therapeutic class for targeting tumor cells and mediating their specific killing.

The present inventors have previously identified through a laborious screen and experimentation a TCRL which exhibit unprecedented fine specificity towards TyrD-HLA-A2 (WO2016/199141). The antibody was termed D11.

Figure 2:
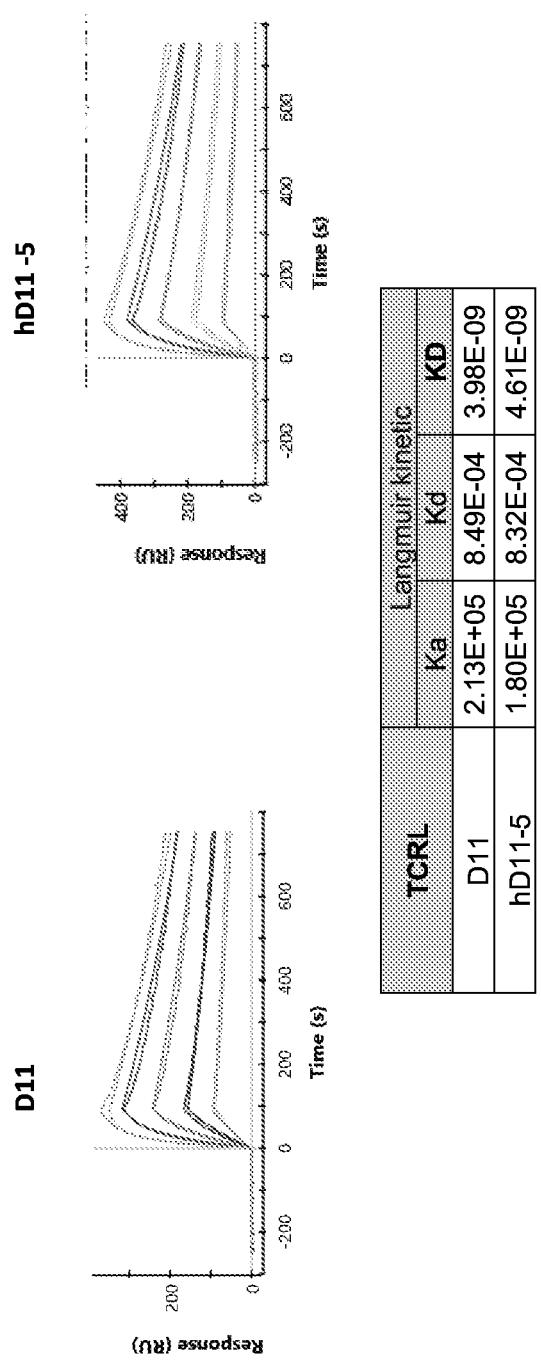
FIG. 2 shows the apparent binding affinity determination of the D11 and hD11-5 TCRL antibodies to HLA-A2/TyrD 369-377 complexes as determined by SPR.
Figure 3:
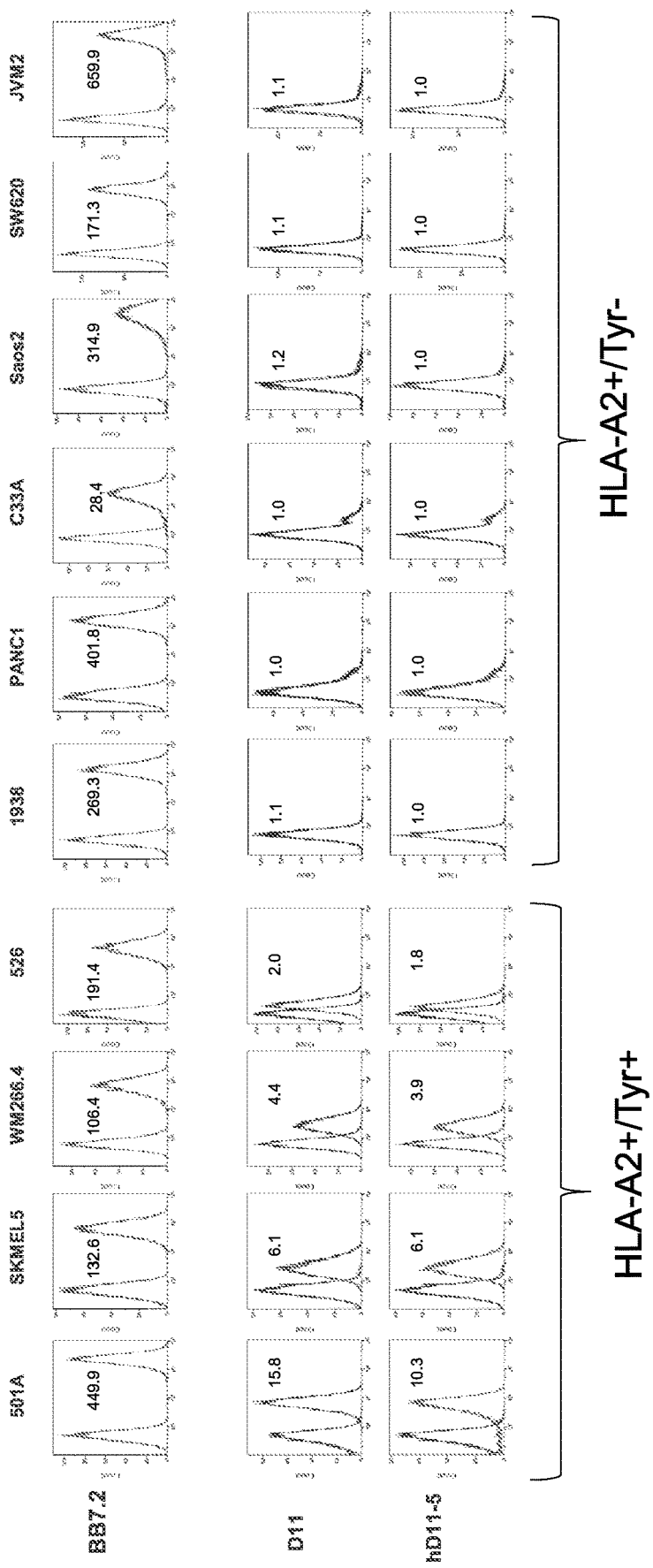
FIG. 3 shows the binding specificity of biotinylated D11 and dH11-5 TCRL antibodies to HLA-A2+/Tyr antigen positive or negative cells.
Figure 4:
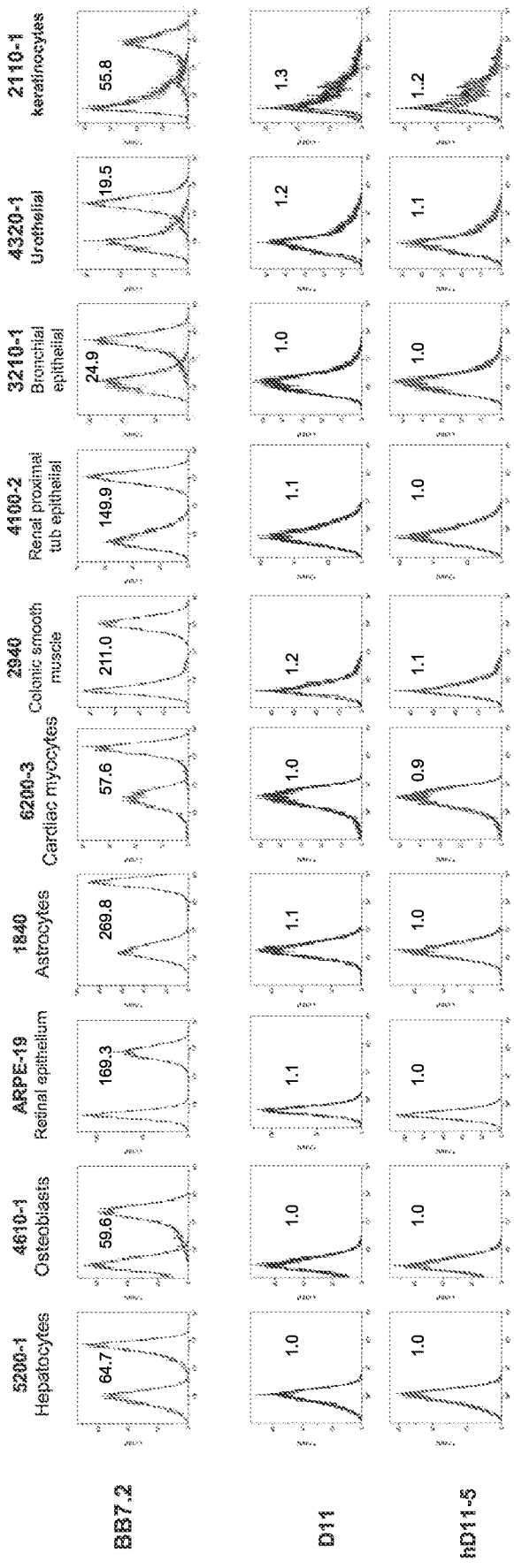
FIG. 4 shows binding of biotinylated D11 and hD11-5 TCRL antibodies to HLA-A2+ primary normal cells.

The present inventors have now successfully humanized D11 and generated a bi-specific configuration thereof having an anti CD3 arm. Following a cumbersome humanization process which included a critical a framework modification in the light chain variable regions (Y49H) a complete humanized antibody termed hD11-5 was obtained. The humanized form maintains all the functional features of D11 including apparent binding affinity and binding specificity (FIGS. 2-4). A bi-specific configuration of the antibody comprising an anti-CD3 arm (termed CD3-ChD11-5) showed potent activity in melanoma cell killing as determined in vitro and in vivo (see FIGS. 5-7).

Altogether, the present findings place hD11-5 as a powerful tool in the treatment of cancer.

Thus, according to an aspect of the invention there is provided an antibody comprising an antigen binding domain comprising CDR sequences which are N—C ordered:

CDR1 Heavy
Chain (HC)
SEQ ID NO: 8
TSGMGVS

CDR2 HC
SEQ ID NO: 9
HIYWDDDKRYNPSLKS

CDR3 HC
SEQ ID NO: 10
KDYGSSFYAMHY

CDR1 Light
Chain (LC)
SEQ ID NO: 5
KASQDIHNYIA

CDR2 LC
SEQ ID NO: 6
YTSTLQP

CDR3 LC
SEQ ID NO: 7
LQYDNLWT wherein a variable region of the heavy chain of the antibody is as set forth in SEQ ID NO: 4 and the antibody is capable of binding HLA-A2/Tyr$_{D369-377}$ in an HLA restricted manner.

Alternatively, there is provided an antibody comprising an antigen binding domain comprising CDR sequences which are N—C ordered:

CDR1 Heavy
Chain (HC)
SEQ ID NO: 8
TSGMGVS

CDR2 HC
SEQ ID NO: 9
HIYWDDDKRYNPSLKS

CDR3 HC
SEQ ID NO: 10
KDYGSSFYAMHY

CDR1 Light
Chain (LC)
SEQ ID NO: 5
KASQDIHNYIA

CDR2 LC
SEQ ID NO: 6
YTSTLQP

CDR3 LC
SEQ ID NO: 7
LQYDNLWT wherein a variable region of the heavy chain of the antibody is as set forth in SEQ ID NO: 4, a variable region of the light chain of the antibody is as set forth in SEQ ID NO: 2 and the antibody is capable of binding HLA-A2/Tyr$_{D369-377}$ in an HLA restricted manner.

As used herein "binding" or "binds" refers to an antibody-antigen mode of binding, which is generally, in the case of clinically relevant TCRLs, and in this case in the range of K$_D$ below 5 nM (e.g., 3.5-4.9 nM), as determined by Surface Plasmon Resonance assay (SPR).

The affinity of the antibody to its antigen is determined by Surface Plasmon Resonance (SPR) using a captured or immobilized monoclonal antibody (MAb) format to minimize contribution of avidity. For affinity evaluation, the antigen is used in its soluble form i.e., single chain (sc) HLA-A2/Tyr$_{D369-377}$ complex as described hereinbelow.

As used herein the term "K$_D$" refers to the equilibrium dissociation constant between the antigen binding domain and its respective antigen.

The term "antibody" as used in this invention includes intact molecules e.g., IgG as well as fragments thereof which include the variable region of the humanized heavy chain i.e., SEQ ID NO: 4.

According to a specific embodiment, the antibody fragments include, but are not limited to, single chain, F$_{ab}$, F$_{ab'}$ and F$_{(ab')2}$ fragments, Fv, dsFv, scFvs, diabodies, minibodies, nanobodies, F$_{ab}$ expression library or single domain molecules such as VH and VL that are capable of binding to an epitope of the antigen in an HLA restricted manner.

As used herein, the "variable regions" and "CDRs" may refer to variable regions and CDRs defined by any approach known in the art, including combinations of approaches. According to a specific embodiment, the CDRs are determined according to Kabat et al. (supra).

According to a specific embodiment, the antibody is a humanized antibody.

According to a specific embodiment, the antibody is a chimeric antibody.

As used herein "a chimeric antibody" refers to an antibody in which at least one chain is of a non-human (e.g., murine) animal and a constant region [e.g., constant region e.g., CL (kappa or lambda)] is human. Thus, for example, the antibody can be a full antibody or a fragment thereof in which both chains comprise non-human variable regions and human constant regions. According to another example, one chain is humanized and another chain comprises non-human variable regions and human constant regions. A bi-specific configuration of a chimeric antibody is described hereinbelow.

Humanized forms of non-human (e.g., murine) antibodies are chimeric molecules of immunoglobulins, immunoglobulin chains which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse in this case, having the desired specificity, affinity and potency (cell killing). In some instances, Fv framework residues of the human immunoglobulin are replaced by corresponding non-human residues. Humanized antibodies may also comprise residues which are found neither in the recipient antibody nor in the imported CDR or framework sequences. The humanized antibody comprises all of the CDR regions corresponding to those of a non-human immunoglobulin and all or substantially all of the FR regions of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

According to a specific embodiment, the antibody comprises the variable region of the light chain as set forth in SEQ ID NO: 2 or 25 and therefore is a humanized antibody.

According to a specific embodiment, the antibody comprises the variable region of the light chain as set forth in SEQ ID NO: 19.

In some embodiments, the immunoglobulin isotype is selected from IgG1, IgG2, IgG3, and IgG4, more particularly, IgG1 or IgG4. According to a specific embodiment, the isotype is IgG1.

According to a specific embodiment the antibody comprises a therapeutic moiety.

According to a specific embodiment, the antibody is a bi-specific antibody.

Thus, bispecific configurations of the hD11-5 antibody are also contemplated herein, either as humanized forms (having variable regions of light and heavy chains as set forth in SEQ ID NO: 2 and SEQ ID NO: 4 respectively) or as chimeric forms (e.g., having variable domains of a light chain as set forth in SEQ ID NO: 19 and heavy chain as set forth in SEQ ID NO: 21). A bispecific antibody (BsAb) is an artificial protein that is composed of fragments of two different monoclonal antibodies and consequently binds to two different types of antigen in this case HLA-A2/TyrD$_{369-377}$ and another epitope distinct of said TyrD$_{369-377}$. According to a specific embodiment the BsAb is engineered to simultaneously bind to a cytotoxic cell such as T cell via CD3 and a target melanoma cell via TyrD HLA-A2-restricted peptide. Other exemplary configurations are described hereinbelow.

As used herein the phrase "MHC (or HLA)-restricted peptide" refers to a peptide which is presented on an HLA molecule, in this case TyrD$_{369-377}$ (abbreviated here as "TyrD" SEQ ID NO: 15) presented on HLA-A2 molecule.

According to a specific embodiment, the scFv of the anti-CD3 is as set forth in SEQ ID NOs: 16, 17, polynucleotide or polypeptide).

According to an aspect of the invention there is also provided an isolated polynucleotide comprising a nucleic acid sequence encoding the antibodies as described herein.

According to a specific embodiment, the nucleic acid sequences encoding the humanized antibody capable of binding TyrD$_{369-377}$ in an HLA-A2 restricted manner are as set forth in SEQ ID NO: 1, 3, 24, 26).

According to a specific embodiment, the nucleic acid sequences encoding a chimeric antibody capable of binding TyrD$_{369-377}$ in an HLA restricted manner are as set forth in SEQ ID NO: 3, 20 or 26 and 18.

According to a specific embodiment, the nucleic acid sequence encoding the anti-CD3 scFv is as set forth in SEQ ID NO: 17.

Also provided is an expression vector, comprising the polynucleotide operably linked to a cis-acting regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion or presentation of antibody from a host cell in which it is placed. Preferably the signal sequence for this purpose is a mammalian signal sequence.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of TCRL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Improvements in recombinant polypeptide expression in mammalian cells can be achieved by effectively increasing the gene dosage in a transfected host cell. Increases in gene copy number are most commonly achieved by gene amplification using cell lines deficient in an enzyme such as dihydrofolate reductase (DHFR) or glutamine synthetase (GS) in conjunction with expression vectors containing genes encoding these enzymes and agents such as methotrexate (MTX), which inhibits DHFR, and methionine sulfoxamine (MSX), which inhibits GS. Thus, in an exemplary embodiment, expression vectors containing the recombinant gene under control of a strong promoter and genes encoding DHFR or GS, DHFR$^+$ or GS.sup$^+$ transfectants, respectively, can be obtained and gene amplification is then achieved by growing the transfectants in progressively increasing concentrations of MTX or MSX0.

Exemplary systems for expression are described in EP2861741, US20120178126, and US20080145895, each of which is incorporated herein by reference in its entirety.

Also provided are cells which comprise the polynucleotides/expression vectors as described herein.

Suitable host cells for cloning or expression of antibody-encoding vectors include prokaryotic or eukaryotic cells described herein. For example, antibodies may be produced in bacteria, in particular when glycosylation and Fc effector function are not needed. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR.sup.-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

The high specificity of the antibody renders it particularly suitable for diagnostic (especially in in vivo diagnosis in which the humanized character of the antibodies is critical) and therapeutic applications.

Thus, according to an aspect of the present invention, there is provided a method of detecting a cell presenting $TyrD_{369-377}$ in an HLA restricted manner. The method comprises contacting the cell with the antibody of the present invention having specificity to the HLA-A2-restricted TyrD peptide antigen. The contacting is effected under conditions which allow immunocomplex formation, wherein a presence of the immunocomplex or level thereof is indicative of the cell presenting the HLA-restricted peptide antigen of interest.

The term "detecting", as used herein, refers to the act of detecting, perceiving, uncovering, exposing, visualizing or identifying a cell. The precise method of detecting is dependent on the detectable moiety (also referred to herein as identifiable moiety) to which the antibody is attached as further described herein below.

The above-mentioned detection method can be harnessed to the diagnosis of cancer e.g., melanoma and glioblastoma characterized by presentation of $TyrD_{369-377}$ in an HLA restricted manner.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being check up. Alternatively, the subject may be at risk of the disease. Yet alternatively, the method may be used to monitor treatment efficacy.

The TCRL may comprise e.g., attached to an identifiable moiety. Alternatively or additionally, the TCRL (or a complex comprising same) may be identified indirectly such as by using a secondary antibody.

As mentioned, the method of the present invention is effected under conditions sufficient to form an immunocomplex (e.g. a complex between the antibodies of the present invention and the peptide complexed to the HLA, typically when the cells are not lysed); such conditions (e.g., appropriate concentrations, buffers, temperatures, reaction times) as well as methods to optimize such conditions are known to those skilled in the art, and examples are disclosed herein.

The antibodies of the invention are especially useful for the treatment of cancer.

The term "cancer" as used herein is defined as disease characterized by the rapid and uncontrolled growth of aberrant cells. Cancer cells can spread locally or through the bloodstream and lymphatic system to other parts of the body.

According to some embodiments of the invention, the pathology is a solid tumor.

According to a specific embodiment, the pathology is melanoma.

According to a specific embodiment, the pathology is glioblastoma.

According to some embodiments of the invention, the antibody of the invention has an anti-tumor effect.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the medicament of the invention in prevention of the occurrence of tumor in the first place.

According to a specific embodiment, when the antibody is for Tyrosinase (TyrD) positive cancer.

The term "TyrD$_{369-377}$-positive cancer" refers to a cancer comprising cells that present TyrD in an HLA-restricted manner. According to a specific embodiment, the TyrD$_{369-377}$-positive cancer is melanoma or glioblastoma.

As used herein "melanoma" refers to a cancer that develops from the pigment-containing cells known as melanocytes. Melanomas typically occur in the skin but may rarely occur in the mouth, intestines, or eye.

Embodiments of the invention refer to melanoma of the following types:
Lentigo maligna
Lentigo maligna melanoma
Superficial spreading melanoma
Acral lentiginous melanoma
Mucosal melanoma
Nodular melanoma
Polypoid melanoma
Desmoplastic melanoma
Melanoma with small nevus-like cells
Melanoma with features of a Spitz nevus
Uveal melanoma
Melanoma cancer staging is available at TNM. Also of importance are the "Clark level" and "Breslow's depth", which refer to the microscopic depth of tumor invasion.
Melanoma stages, each of which is contemplated herein.
Stage 0: Melanoma in situ (Clark Level I), 99.9% survival
Stage I/II: Invasive melanoma, 89-95% survival
T1a: Less than 1.0 mm primary tumor thickness, without ulceration, and mitosis <1/mm2
T1b: Less than 1.0 mm primary tumor thickness, with ulceration or mitoses ≥1/mm2
T2a: 1.01-2.0 mm primary tumor thickness, without ulceration
Stage II: High risk melanoma, 45-79% survival
T2b: 1.01-2.0 mm primary tumor thickness, with ulceration
T3a: 2.01-4.0 mm primary tumor thickness, without ulceration
T3b: 2.01-4.0 mm primary tumor thickness, with ulceration
T4a: Greater than 4.0 mm primary tumor thickness, without ulceration
T4b: Greater than 4.0 mm primary tumor thickness, with ulceration
Stage III: Regional metastasis, 24-70% survival
N1: Single positive lymph node
N2: Two to three positive lymph nodes or regional skin/in-transit metastasis
N3: Four positive lymph nodes or one lymph node and regional skin/in-transit metastases
Stage IV: Distant metastasis, 7-19% survival
M1a: Distant skin metastasis, normal LDH
M1b: Lung metastasis, normal LDH
M1c: Other distant metastasis or any distant metastasis with elevated LDH
Based upon AJCC five-year survival from initial melanoma diagnosis with proper treatment.

As used herein "glioblastoma" or "glioblastoma multiforme (GBM)" refers to the most aggressive cancer that begins within the brain.

According to a specific embodiment, the glioblastoma can be classified as follows:

Classical: Ninety-seven percent of tumors in the 'classical' subtype carry extra copies of the epidermal growth factor receptor (EGFR) gene, and most have higher than normal expression of epidermal growth factor receptor (EGFR), whereas the gene TP53 (p53), which is often mutated in glioblastoma, is rarely mutated in this subtype.

The Proneural subtype often has high rates of alterations in TP53 (p53), and in PDGFRA, the gene encoding a-type platelet-derived growth factor receptor, and in IDH1, the gene encoding isocitrate dehydrogenase-1.

The Mesenchymal subtype is characterized by high rates of mutations or other alterations in NF1, the gene encoding Neurofibromin 1 and fewer alterations in the EGFR gene and less expression of EGFR than other types.

The Neural subtype was typified by the expression of neuron markers such as NEFL, GABRA1, SYT1 and SLC12A5.

Many other genetic alterations have been described in glioblastoma, and the majority of them are clustered in two pathways, the RB and the PI3K/AKT. Glioblastomas have alterations in 68-78% and 88% of these pathways, respectively.

Another important alteration is methylation of MGMT, a "suicide" DNA repair enzyme. Methylation is described to impair DNA transcription and therefore, expression of the MGMT enzyme. Since an MGMT enzyme can only repair one DNA alkylation due to its suicide repair mechanism, reverse capacity is low and methylation of the MGMT gene promoter greatly affects DNA-repair capacity.[35][36] Indeed, MGMT methylation is associated with an improved response to treatment with DNA-damaging chemotherapeutics, such as temozolomide.

In either case, according to some embodiments, the cancer is characterized by expression of Tyrosinase mRNA or protein (e.g., as determined using methods which are well known in the art such as by RT-PCR or immunohistochemistry).

The foregoing classifications are relevant for both diagnosis and treatment.

Determining a presence or level of the immunocomplex of the present invention is dependent on the detectable moiety to which the antibody is attached.

Examples of detectable moieties that can be used in the present invention include but are not limited to radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

Further examples of detectable moieties, include those detectable by Positron Emission Tomography (PET) and Magnetic Resonance Imaging (MRI), all of which are well known to those of skill in the art.

When the detectable moiety is a polypeptide, the immunolabel (i.e. the antibody conjugated to the detectable moiety) may be produced by recombinant means or may be chemically synthesized by, for example, the stepwise addition of one or more amino acid residues in defined order using solid phase peptide synthetic techniques. Examples of polypeptide detectable moieties that can be linked to the antibodies of the present invention using recombinant DNA technology (in which the polynucleotide encoding the TCRL is translationally fused to the detectable moiety) include fluorescent polypeptides, phosphorescent polypeptides, enzymes and epitope tags.

Alternatively, chemical attachment of a detectable moiety to the antibodies of the present invention can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Thus, the conjugates described herein can be prepared by known methods of linking antibodies with lipids, carbohydrates, protein, toxins, drugs or other atoms and molecules. In some embodiments, the conjugate is formed by site-specific conjugation using a suitable linkage or bond. Site-specific conjugation is more likely to preserve the binding activity of the antibody. The substance may be conjugate or attached at the hinge region of a reduced antigen binding construct via thioether bond formation. In some embodiments, tyrosine conjugation can be employed. Other linkages or bonds used to form the conjugate can include, but are not limited to, a covalent bond, a non-covalent bond, a disulfide linkage, a hydrazone linkage, an ester linkage, an amido linkage, and amino linkage, an imino linkage, a thiosemicarbazone linkage, a semicarbazone linkage, an oxime linkage and a carbon-carbon linkage. In some embodiments, no cysteine or other linking aspect, need be included in antibody (Bioconjugate Techniques (Third Edition) Author(s): Greg T. Hermanson ISBN: 978-0-12-382239-0).

Exemplary methods for conjugating moieties are described in WO2017/027325 or U.S. Pat. No. 9,078,931 each of which is hereby incorporated by reference in its entirety.

As mentioned the antibodies of the present invention can also be used in therapeutics.

In a whole antibody, a therapeutic activity is intrinsic to the molecule since the Fc domain activates antibody-dependent cell-mediated cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. For example, eosinophils can kill certain parasitic worms known as helminths through ADCC mediated by IgE. ADCC is part of the adaptive immune response due to its dependence on a prior antibody response.

Alternatively or additionally and as mentioned, the antibody may be a bispecific antibody in which the therapeutic moiety is a T cell engager for example, such as an anti CD3 antibody or an anti CD16a alternatively the therapeutic moiety may be an anti immune checkpoint molecule (e.g. anti PD-1, anti-PD-L1, anti-CTLA4). According to a specific embodiment, the therapeutic moiety is anti CD3.

Alternatively or additionally the antibody may be attached to a heterologous therapeutic moiety (methods of conjugation are described hereinabove). The therapeutic moiety can be, for example, a cytotoxic moiety, a toxic moiety, a cytokine moiety, a drug. Examples include, but are not limited to, BRAF inhibitors such as vemurafenib and dabrafenib as well as radioisotopes or toxins e.g., purothionin, pseudomonas exotoxin A, methotrexate.

The antibody may be in a soluble or insoluble form.

Insoluble forms may be those in which a molecule comprising the humanized antibody's variable regions are expressed by a cell (i.e., also referred to herein as the therapeutic moiety).

Examples of such cells include immune cells, T cells, B cells, dendritic cells, CIK, NKT, NK cells (autologous, allogeneic, xenogeneic).

According to a specific embodiment, the antibody (or variable regions thereof thereof) form a CAR or an artificial T Cell Receptor.

The term "chimeric antigen receptors (CARs)," as used herein, may refer to artificial T-cell receptors, T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain (allowing the T cell to activate upon engagement of targeting moiety with target cell, such as a target tumor cell), a transmembrane domain, and an extracellular domain that may vary in length and comprises a disease- or disorder-associated, e.g., a tumor-antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP 10/12, and/or OX40, ICOS, TLRs, etc. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

In certain embodiments, an αβ T-cell, γδ T-cell, NK, macrophage, or B cell, or cell population(s) of some embodiments of the invention are engineered to stably express one or more structurally distinct antibodies encoded by expression cassettes. The antibody may be selected from the group consisting of a chimeric antigen receptor (CAR), whole antibody or their antigen-binding fragment, single-chain variable fragment (scFv), a heavy chain or a light chain single domain antibody (sdAb), a Fab, a F(ab)$_2$, or any combination thereof that binds to: (i) a cell surface tumor antigen or (ii) a peptide derived from a tumor antigen expressed on the cell surface as a complex with MHC (peptide-MHC complex).

Thus a polynucleotide coding for such a molecule is transduced in a cell of interest (e.g., SEQ ID NOs. 1, 3 or any polynucleotide encoding SEQ ID NOs: 2, 4).

According to some embodiments of the invention, the cell is a T cell, a natural killer cell, a cell that exerts effector killing function on a target cell, a cell that exerts a suppressive effect on effector T cells, an engineered cell with an effector killing function or an engineered cell with a suppressive function.

According to some embodiments of the invention, the cell is a T cell, or αβ T cell, or γδ T cell.

According to some embodiments of the invention, the cell is a natural killer (NK) cell.

According to some embodiments of the invention, the natural killer cell is used to target cancer.

According to some embodiments of the invention, the T cell is a cytotoxic T cell (effector T cell).

According to some embodiments of the invention, the cytotoxic T cell (effector T cell) is used to target cancer antigens in this case TyrD.

According to some embodiments of the invention, the T cell comprises a Treg (T regulatory cell).

According to some embodiments of the invention, the T cell comprises a CD3 T cell.

According to some embodiments of the invention, the T cell comprises a CD4 T cell.

According to some embodiments of the invention, the T cell comprises a CD8 T cell.

According to some embodiments of the invention, the antibody is a single chain Fv (scFv) molecule.

The cytoplasmic domain (also referred to as "intracellular signaling domain") of the CAR molecule of the invention is responsible for activation of at least one of the normal effector functions of the immune cell in which the CAR has been placed in.

The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR molecule of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs (ITAMs).

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A co-stimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

According to some embodiments of the invention, the intracellular domain comprises, a co-stimulatory signaling region and a zeta chain portion. The co-stimulatory signaling region refers to a portion of the CAR molecule comprising the intracellular domain of a co-stimulatory molecule. Co-stimulatory molecules are cell surface molecules other than antigen receptors or their ligands that are required for an efficient response of lymphocytes to antigen.

"Co-stimulatory ligand," as the term is used herein, includes a molecule on an antigen presenting cell [e.g., an aAPC (artificial antigen presenting cell), dendritic cell, B cell, and the like] that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

A "co-stimulatory signal", as used herein, refers to a signal, which in combination with a primary signal, such as TCR/CD3 ligation, leads to T cell proliferation and/or upregulation or down regulation of key molecules.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter cilia, an MHC Class I molecule loaded with a peptide, an anti-CD3 antibody, a superagonist anti-CD28 antibody, and a superagonist anti-CD2 antibody.

With respect to the cytoplasmic domain, the CAR molecule of some embodiments of the invention can be designed to comprise the CD28 and/or 4-1BB signaling domain by itself or be combined with any other desired cytoplasmic domain(s) useful in the context of the CAR molecule of some embodiments of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof.

According to some embodiments of the invention, the intracellular domain comprises at least one, e.g., at least two, at least three, at least four, at least five, e.g., at least six of the polypeptides selected from the group consisting of: CD3 (CD247, CD3z), CD28, 41BB, ICOS, OX40, and CD137.

According to some embodiments of the invention, the intracellular domain comprises the CD3ζ-chain [CD247 molecule, also known as "CD3-ZETA" and "CD3z"; GenBank Accession NOs. NP_000725.1 and NP_932170.1], which is the primary transmitter of signals from endogenous TCRs.

According to some embodiments of the invention, the intracellular domain comprises various co-stimulatory protein receptors to the cytoplasmic tail of the CAR to provide additional signals to the T cell (second generation CAR). Examples include, but are not limited to, CD28 [e.g., GenBank Accession Nos. NP_001230006.1, NP_001230007.1, NP_006130.1], 4-1BB [tumor necrosis factor receptor superfamily, member 9 (TNFRSF9), also known as "CD137", e.g., GenBank Accession No. NP_001552.2], and ICOS [inducible T-cell co-stimulator, e.g., GenBank Accession No. NP_036224.1]. Preclinical studies have indicated that the second generation of CAR designs improves the antitumor activity of T cells.

According to some embodiments of the invention, the intracellular domain comprises multiple signaling domains, such as CD3z-CD28-41BB or CD3z-CD28-OX40, to further augment potency. The term "OX40" refers to the tumor necrosis factor receptor superfamily, member 4 (TNFRSF4), e.g., GenBank Accession No. NP_003318.1 ("third-generation" CARs).

According to some embodiments of the invention, the intracellular domain comprises CD28-CD3z, CD3z, CD28-CD137-CD3z. The term "CD137" refers to tumor necrosis factor receptor superfamily, member 9 (TNFRSF9), e.g., GenBank Accession No. NP_001552.2.

According to some embodiments of the invention, when the CAR molecule is designed for a natural killer cell, then the signaling domain can be CD28 and/or CD3ζ. The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

According to some embodiments of the invention, the transmembrane domain comprised in the CAR molecule of some embodiments of the invention is a transmembrane domain that is naturally associated with one of the domains in the CAR. According to some embodiments of the invention, the transmembrane domain can be selected or modified by amino acid substitution to avoid binding of such domains to the transmembrane domains of the same or different surface membrane proteins to minimize interactions with other members of the receptor complex.

According to some embodiments, between the extracellular domain and the transmembrane domain of the CAR molecule, or between the cytoplasmic domain and the transmembrane domain of the CAR molecule, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Any of the above configurations can be used in therapy.

According to an aspect of some embodiments of the invention, there is provided a method of treating cancer in a subject in need thereof, comprising administering to the subject the antibody as described herein, thereby treating the cancer in the subject.

Also provided is a use of the antibody as defined herein in the manufacture of a medicament for treating a pathology e.g., cancer.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology.

The antibodies of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a specific embodiment, the administration comprises intravenous administration.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (TCRL-antibody) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide TCRL or TCRL containing entity such as a cell (the TCRL tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit (diagnostic or therapeutic), which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Ct. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Humanization of D11 TCRL Antibody Using the CDR Grafting

D11 (SEQ ID NOs: 11-14 having CDRs set forth in SEQ ID Nos: 5-10, determined according to Kabat), a murine monoclonal antibody to HLA-A2/TyrD 369-377 (SEQ ID NO: 15) peptide-HLA complex was humanized using complementarity determining region (CDR) grafting on human Ig framework regions. Human frameworks for heavy and light chains were selected based on sequence and structure similarity with respect to functional human germline genes. In this regard, structural similarity was evaluated by comparing the mouse canonical CDR structure to human candidates with the same canonical structures.

D11 was humanized using a computer-aided CDR-grafting method (Abysis Database, UCL Business Plc.) and molecular engineering techniques to provide hD11-5. Molecular engineering procedures were conducted using art-recognized techniques. To that end accurate determination of the murine antibody variable region DNA sequences, amplified by RT-PCR, and homology modeling of its heavy and light chains protein translation were the starting points.

A single framework change was necessary to maintain the favorable properties of the binding of D11. In this respect, there were no framework changes or back mutations made in the heavy chain variable regions and only a single framework modification was undertaken in the light chain variable regions (Y49H in hD11-5). The Y49H back mutation was critical to restore full binding of humanized antibody to HLA-A2/TyrD$_{369-377}$ complex. The amino acid and nucleotide sequences of humanized D11 antibody (hD11-5) are shown in FIG. 1 (SEQ ID NOs: 24-27).

Following humanization of all selected antibodies by CDR grafting, the resulting light and heavy chain variable region amino acid sequences were analyzed to determine their homology with regard to the murine donor and human acceptor light and heavy chain variable regions.

Example 2

Cloning of hD11-5 TCRL Antibody into a Human IgG1 Expression Vectors Followed by Expression and Purification in Expi293 System Synthetic DNA fragments of the humanized heavy and light variable chains of hD11-5 were cloned into a pCI expression vectors containing hIgG1 constant heavy and light chain regions as shown in FIG. 1. The hD11-5 antibody was then expressed by co-transfection of the derived heavy and the light chains constructs into Expi293 cells (ThermoFisher A14635). Signal sequences were included to mediate secretion (SEQ ID NO: 36, 37 for the light chain and SEQ ID NO: 38, 39 for the heavy chain).

Briefly, directional cloning of humanized variable region genes into selected human immunoglobulin expression vectors was done. All primers used in Ig gene-specific PCRs included restriction sites which allowed direct cloning into expression vectors containing human IgG1 heavy chain and light chain constant regions. Synthetic genes digested with AgeI and XhoI (for the heavy chain) and XmaI and DraIII (for the light chain) were purified prior to ligation into expression vectors. Ligation reactions were performed in a total volume of 10 µL with 200 U T4-DNA Ligase (New England Biolabs), 7.5 µL of digested and purified gene-specific PCR product and 25 ng linearized vector DNA. Electro-Competent *E. coli* DH10B bacteria (Life Technologies) were transformed via electroporation (BioRad) with 1 µL ligation product plated onto ampicillin plates (100 µg/mL). The AgeI-XhoI fragment of the VH region was cloned into the same sites of pCI-HuIgG1 expression vector while the synthetic XmaI-DraIII VK insert was cloned into the XmaI-DraIII sites of the respective pCI-Hu-Kappa expression vector.

Plasmid DNA was purified with QIAprep Spin columns (Qiagen). Expi293 cells were cultured in DMEM Medium supplemented with 2% FBS.

For transient transfections, Expi293 cells were grown to 2.5 million cells per ml. Equal amounts of IgH and corresponding IgL chain vector DNA (15 µg of each) were added to 1.5 mL Opti-MEM Medium mixed with 80 µL Expi-Fectamine 293 Reagent in 1.5 mL Opti-MEM Medium (ThermoFisher 31985062). The mix was incubated for 30 min at room temperature and distributed evenly to the 10-cm tissue culture plate (Corning). Supernatants were harvested three days after transfection, replaced by 20 mL of fresh DMEM supplemented with 10% FBS and harvested again at day 6 after transfection. Culture supernatants were cleared of cell debris by centrifugation at 800×g for 10 min. Recombinant humanized antibody hD11-5 was purified using Protein A affinity chromatography (GE Healthcare) or used as a supernatant.

Example 3

Cloning and Expression of D11 TCRL Antibody in Expi293 System

Mouse parental D11 (IgG1 isotype) heavy and light chains (SEQ ID NOs: 11-14) were cloned individually into pCDNA3.4 expression vector by Life Technologies, GeneArt. A leader sequence (SEQ ID NO: 34, 35) was included inframe to mediate secretion.

For transient transfections, Expi293 cells were grown in Expi293 expression medium (Gibco, Cat. A14351-01) to 2.5 million cells per ml in Erlenmeyer flask (Thermo scientific, Cat. 4115-1000), Orbital Shaker (125rpm), 37° C. incubator, 8% CO2. Equal amounts of IgH and corresponding IgL chain vector DNA (375 µg of each) were added to 37.5 mL Opti-MEM Medium (Gibco, Cat. 31985-047). 2.0 ml Expi-Fectamine 293 Reagent (Gibco, Cat. 100014994) was added to Opti-MEM Medium in final volume of 37.5 mL. The two solutions were mixed and incubated for 30 min at room temperature. 25 ml of the mix was added to 212.5 ml cell culture per 1 liter Erlenmeyer flask, total 3 flasks. 16-18 hours post transfection, ExpiFectamine 293 transfection Enhancer 1 (Gibco, Cat. 100013863) and Enhancer 2 (Gibco, Cat. A14350-01) were added (1.25 ml and 12.5 ml per flask, respectively). Six days after transfection cells were harvested by centrifugation at 700×g for 5 min and supernatants were collected, filtered and stored at 4° C. Recombinant mouse antibody was purified with Protein A Mabselect Hitrap extra column (GE Healthcare) and stored under appropriate conditions.

Example 4

Affinity of hD11-5 TCRL Antibody Binding as Determined by SPR Production of Single-Chain HLA-Peptide Complexes Single-chain HLA-A2 (scHLA-A2)/TyrD 369-377 peptide complexes were produced by in vitro refolding of inclusion bodies produced in *Escherichia coli* upon isopropyl β-D-thiogalactoside (IPTG) induction, as described in details in Denkberg, et al. (2000) *Eur. J. Immunol.* 30, 3522-3532. Briefly, a scHLA, which contains the $\beta_2$-microglobulin and the extracellular domains of the HLA-A2 gene connected to each other by a flexible linker was engineered. In vitro refolding was performed in the presence of TyrD 369-377 (SEQ ID NO: 15) peptide. Correctly folded HLA-peptide complexes were isolated and purified by anion exchange Q-Sepharose chromatography (GE Healthcare Life Sciences).

To determine the apparent affinity of the hD11-5 as compared to the parental D11 TCRL antibody, surface plasmon resonance (SPR) binding analysis was performed in which the IgG TCRL antibody was captured by anti-mouse or anti-human antibodies immobilized on the chip surface. Purified single-chain recombinant HLA-A2/TyrD 369-377 peptide complex was used as the analyte. Briefly, six channels of ProteOn GLM sensor chip (BioRad laboratories) were activated with 50 μl of a mixture of 0.04 M N-ethyl-N'-(3-dimethylaminopropyl) carbodiimide (EDC) and 0.01 M sulfo-N-hydroxysuccinimide (Sulfo-NHS) at a flow rate of 30 μl/min. The anti-mouse or anti-human polyclonal antibodies (Jackson ImmunoResearch) were diluted in 10 mM sodium acetate buffer pH 4.5 to a final concentration of 25 μg/ml and 150 μl were injected followed by an injection of 150 μl of 1 M ethanolamine-HCl pH 8.5. The IgG TCRL antibodies were injected in the vertical orientation with a flow rate of 30 μl/min. The purified single-chain recombinant HLA-A2/TyrD 369-377 peptide complex was injected in the horizontal orientation of the ProteOn using five different concentrations (250, 125, 62.5, 31.2 and 16 nM). Running buffer (PBST) was injected simultaneously in the sixth channel for double referencing to correct for loss of the captured antibodies from the chip sensor surface during the experiment. All binding sensorgrams were collected, processed and analyzed using the integrated ProteOn Manager (Bio-Rad Laboratories, Hercules, USA) software. Binding curves were fitted using the Langmuir model describing 1:1 binding stoichiometry, or with the Langmuir and mass transfer limitation model. As shown in FIG. 2, both hD11-5 and D11 TCRL antibodies demonstrated similar affinity to the HLA-A2/TyrD 369-377 peptide complex of 3.9 and 4.6 nM respectively.

Example 5

Selectivity and Specificity of the hD11-5 TCRL Antibody

Selectivity and specificity of hD11-5 binding to HLA-A2/TyrD 369-377 complex was demonstrated by flow cytometry on a panel of HLA-A2+ cell lines and primary cells. WM266.4 cell line (CRL-1676, ATCC) was cultured in complete DMEM supplemented with 10% FBS (all supplied by GIBCO). C33A cell line (HTB-31, ATCC) was cultured in complete EMEM supplemented with 10% FBS (all supplied by GIBCO). 501A, Mel526, SKMel5 (HTB-70, ATCC), Mewo (HTB-65, ATCC) and 1938 (melanoma), Saos2 (HTB-85, osteosarcoma from ATCC), Panc1 (CRL-1469, pancreatic carcinoma from ATCC), J82 (HTB-1, ATCC), JVM2 (CRL-3002, Mantle cell lymphoma from ATCC), and SW620 (CCL-227, colorectal adenocarcinoma from ATCC) cell lines were cultured in complete RPMI supplemented with 10% FBS (all supplied by GIBCO). Malme3M (HTB-64, melanoma from ATCC) and Y79 (HTB-18, retinoblastoma from ATCC) cell lines were cultured in complete RPMI supplemented with 20% FBS (all supplied by GIBCO). Cell lines were maintained at 37° C. in a humidified atmosphere of 7.5% $CO_2$.

Normal primary keratinocytes, hepatocytes, cardiac myocytes, osteoblasts, astrocytes, bronchial epithelial cells, colonic smooth muscle cells, urothelial cells and renal epithelial cells were obtained from Sciencell. Retinal epithelium (ARPE-19) cells were obtained from ATCC (CRL-2302). Cells were cultured according to the manufacturer's instructions and maintained at 37° C. in a humidified atmosphere of 7.5% $CO_2$.

Briefly, Tyr+ (501A, SKMELS, WM266.4, 526) and Tyr− (1938, PANC1, C33A, SAOS2, SW620, JVM2) cell lines were incubated with 10 μg/ml of biotinylated hD11-5 and D11 TCRL antibodies for 1 h at 4° C., followed by incubation with PE-labeled streptavidin conjugate for 45 min at 4° C. BB7.2 antibody (10 μg/ml) was used to monitor expression of HLA-A2 using secondary PE-labeled anti-mouse IgG.

As shown in FIG. 3 biotinylated hD11-5 and D11 TCRL antibodies specifically stained HLA-A2+/Tyr positive cells. No reactivity was detected on multiple HLA-A2+/Tyr negative cell lines. BB7.2 antibody staining confirmed HLA-A2+ status of the cell lines in this panel.

The biotinylated hD11-5 and D11 TCRL antibodies reactivity was also tested on a panel of normal primary cells including astrocytes, hepatocytes, renal cells, cardiac myocytes, colonic muscle, bronchial epithelial, osteoblasts, bronchial, keratinocytes and normal retinal pigment epithelial cell line ARPE19 (FIG. 4). No binding to these HLA-A2+ cells was observed. BB7.2 antibody staining confirmed HLA-A2+ status of the cells in this panel.

Example 6

Generation and Functional Characterization of Chimeric Bispecific TCRL CD3-ChD11-5 in Cytotoxicity Assays The variable region of the humanized heavy chain and human constant region 1 (VH-CH1) and the variable region of the murine light chain (VL) and human constant kappa chain (CL) of D11 (SEQ ID NO 20 and SEQ ID NO 18) were assembled with an anti-CD3 scFv fragment (SEQ ID NO: 16), into a bi-specific construct, which can re-target effector T cells to HLA-A2+/Tyr369-377+ target cells. Briefly, anti-CD3 scFv was fused to N-terminus of chimeric light chain (mouse-VL human-CL kappa) via a connector (SEQ ID NO: 32, 33) and 6xHis-Tag was added to the C-terminus of VH-CH1 (SEQ ID NO: 20, 21) domain of hD11-5. A leader sequence (SEQ ID NO: 34, 35) was included in-frame. Both constructs were cloned into pcDNA3.4 vector for expression in mammalian cells to yield a bi-specific antibody termed, CD3-ChD11-5 BS.

CD3-ChD11-5 BS TCRL was expressed by co transfection of the two constructs into the Expi293F human cells as described in Example 3. After 6 days in culture cells were centrifuged at 700xg for 5 minutes, the supernatant containing the CD3-ChD11-5 BS TCRL antibody was harvested, filtered and dialyzed. The CD3-ChD11-5 BS TCRL recombinant protein was purified by metal affinity (Talon) and size exclusion chromatography (Superdex 200 10/300 GL GE).

Cytotoxicity was measured in a non-radioactive assay using CytoTox96® (Promega). This assay quantitatively measures lactate dehydrogenase (LDH), an enzyme that is released upon cell lysis. Released LDH in culture supernatants is measured with a 10 minute coupled enzymatic assay, which results in the conversion of a tetrazolium salt (INT) into a red formazan product. The amount of color produced is proportional to the number of lysed cells.

Specifically, target cells and effector cells were washed, counted and resuspended in cRPMI medium (1% FBS) without phenol red. Target cells were adjusted to a cell density of $2.5\times10^5$ cells per ml and the effector cells at a cell density of $2.5\times10^6$ cells per ml. 40 µl ($1\times10^4$ cells) of target cells were cultured in a 96-well V-shaped plate. A 5×stock of the CD3-ChD11-5 BS TCRL test reagent was prepared at the highest test concentration, and then serially diluted 1:10 in a medium without phenol red in a separate plate to obtain other test concentrations. The CD3-ChD11-5 and CD3-D11 BS TCRL were then added to the target cells in the assay plate at 20 µl per well to give the final indicated titrated amounts. The assay plate containing the target cells mixed with the BSs TCRL was then incubated for 20 minutes at 37° C./5% $CO_2$. Following the incubation, 40 µl effector cells ($1\times10^5$ cells) were added to each well resulting in an effector to target (E:T) ratio of 10:1. Control wells were set up with effector cells alone to calculate effector spontaneous release, target cells alone to calculate target spontaneous release, and target cells with 80 µg/ml digitonin final to calculate maximum release. Each condition was assayed in triplicates in a final volume of 100 µl. The plate was incubated at 37° C./5% $CO_2$ for 24 hours. Following the incubation period, the plate was centrifuged at 700×g for 5 minutes and 50 µl transferred from each well to the corresponding well in a 96-well flat bottomed Maxisorb plate (Nunc). The CytoTox96® substrate mix was reconstituted using CytoTox96® assay buffer, as per manufacturer's instructions, and 50 µl added to each well of the plate. The plate was covered with aluminum foil and incubated at room temperature for 10 minutes. Then absorbance recorded at 490 nm on a plate reader. Percentage cytotoxicity was then calculated using the following equation: Specific lysis=[(Experimental−Effector Spontaneous−Target Spontaneous)/(Target Maximum−Target Spontaneous)]×100. PBMCs for killing assays are isolated from healthy volunteers and with all regulatory IRBs approvals and written consents. Effector PBMCs are isolated using the Lymphoprep procedure.

Figure 6:
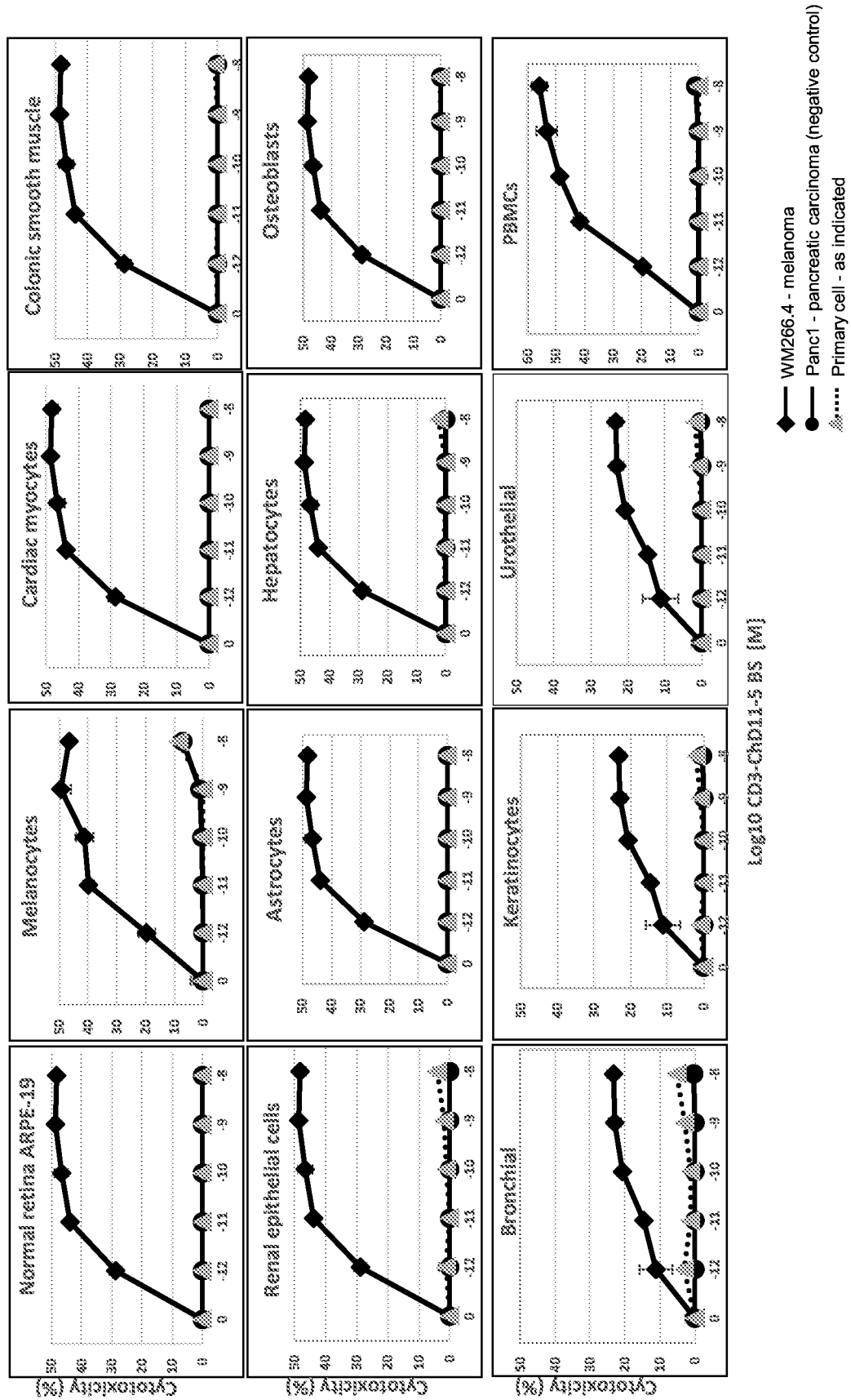
FIG. 6 shows killing of HLA-A2+ normal primary cells and normal retinal pigment epithelial cell line (ARPE-19) by CD3-ChD11-5 BS TCRL.

As shown in FIGS. 5A-B and 6, CD3-chD11-5 BS TCRL demonstrated cytotoxicity against melanoma WM266.4 cells in vitro in the presence of human PBMCs. Panc-1, HLA-A2+/Tyr− cell line served as negative control and showed no cytotoxicity. Cytotoxicity was also detected against a panel of HLA-A2+/Tyr+ melanoma cell lines (FIG. 5A). No cytotoxicity was detected against a panel of HLA-A2+/Tyr− cell lines (FIG. 5B) and normal human primary cells (FIG. 6) with the CD-ChD11-5 BS TCRL confirming its selectivity.

Example 7

Anti-Tumor Activity of CD3-ChD11-5 BS TCRL and CD3-D11 BS TCRL in Established Melanoma Xenograft Mouse Model Mel526 melanoma cell line was cultured in RPMI1640 growth medium (GIBCO, Waltham Mass., USA) supplemented with 10% fetal bovine serum (GIBCO, Waltham Mass., USA). Human peripheral blood mononuclear cells (PBMC) were prepared from healthy donors and CD3 positive cells were expanded ex-vivo and used as effector cells as described in WO2016/19914 1, which is hereby incorporated by reference in its entirety.

At day 0, six to eight weeks old female NOD/SCID mice (Envigo, Israel) were inoculated subcutaneously (s.c.) in a single flank with $5\times10^6$ Mel526 melanoma cells with or without $15\times10^6$ ex vivo expanded effector PBMCs (Effector: Tumor cell ratio 3:1) in a final volume of 0.1 ml of 50% Matrigel® (Corning). Once palpable tumors were established on Day 5, mice were treated i.v. with CD3-D11, CD3-ChD11-5 or CD3-Control BS TCRL at 15 µg/mouse dosage or with vehicle control (PBS) in a final volume of 0.1 ml, with 5 additional doses administered every 24 hours for a total of 6 doses.

Figure 7:
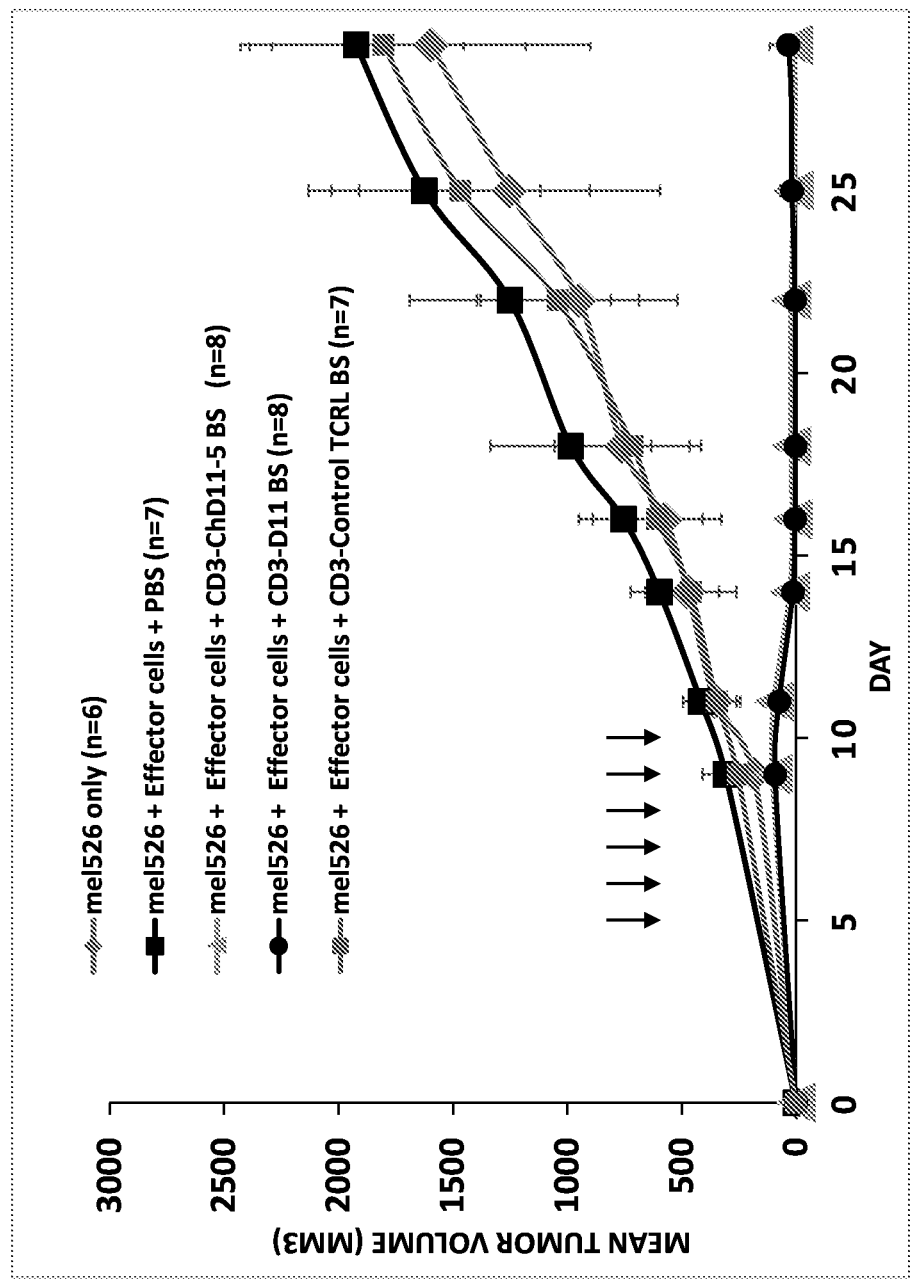
FIG. 7 shows anti-tumor activity of CD3-D11 and CD3-ChD11-5 BS TCRLs in established human melanoma xenograft model Mel526.

FIG. 7 shows that both CD3-ChD11-5 and CD3-D11 BS TCRL induced tumor regression in this model over a period of 29 days.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody comprising an antigen binding domain comprising CDR sequences which are N—C ordered:

CDR1 Heavy
Chain (HC)
                                SEQ ID NO: 8
TSGMGVS

CDR2 HC
                                SEQ ID NO: 9
HIYWDDDKRYNPSLKS

CDR3 HC
                                SEQ ID NO: 10
KDYGSSFYAMHY

CDR1 Light
Chain (LC)
                                SEQ ID NO: 5
KASQDIHNYIA

CDR2 LC
                                SEQ ID NO: 6
YTSTLQP

CDR3 LC
                                SEQ ID NO: 7
LQYDNLWT wherein a variable region of said heavy chain of the antibody is as set forth in SEQ ID NO: 4 and said antibody is capable of binding HLA-A2/Tyr$_{D369-377}$ in an HLA restricted manner.

2. An antibody comprising an antigen binding domain comprising CDR sequences which are N—C ordered:

CDR1 Heavy
Chain (HC)
                                SEQ ID NO: 8
TSGMGVS

CDR2 HC
                                SEQ ID NO: 9
HIYWDDDKRYNPSLKS

CDR3 HC
                                SEQ ID NO: 10
KDYGSSFYAMHY

CDR1 Light
Chain (LC)
                                SEQ ID NO: 5
KASQDIHNYIA

CDR2 LC
                                SEQ ID NO: 6
YTSTLQP

CDR3 LC
                                SEQ ID NO: 7
LQYDNLWT wherein a variable region of said heavy chain of the antibody is as set forth in SEQ ID NO: 4, a variable region of said light chain of the antibody is as set forth in SEQ ID NO: 2 and said antibody is capable of binding HLA-A2/Tyr$_{D369\text{-}377}$ in an HLA restricted manner.

3. The antibody of claim 1 or 2, wherein said antibody is an IgG antibody.

4. The antibody of claim 1, wherein said antibody is a chimeric antibody.

5. The antibody of claim 1 or claim 2, wherein said antibody is an antibody fragment.

6. The antibody of claim 5 selected from the group consisting of Fab, F(ab')2, Fv, scFv, dsFv and a single domain molecule.

7. The antibody of claim 1 or claim 2, wherein said heavy chain of the antibody is as set forth in SEQ ID NO: 21 or 27.

8. The antibody of claim 1, wherein said light chain of the antibody is as set forth in SEQ ID NO: 2, 19 or 25.

9. The antibody of claim 1 or claim 2 comprising a therapeutic moiety.

10. The antibody of claim 9, wherein said therapeutic moiety is selected from the group consisting of a cytotoxic moiety, a toxic moiety, a cytokine moiety and a drug.

11. The antibody of claim 9, wherein said therapeutic moiety comprises a cell.

12. The antibody of claim 11, wherein said cell is selected from the group consisting of an αβ T-cell, γδ T-cell, NK, CIK, NKT, macrophage and a B cell.

13. The antibody of claim 1 or claim 2, wherein said antibody is a bispecific antibody.

14. The antibody of claim 13, wherein said bispecific antibody comprises an anti-CD3 or an anti-CD16.

15. The antibody of claim 14, wherein said anti-CD3 comprises an scFv.

16. A chimeric antigen receptor comprising the antibody according to claim 1 or claim 2.

17. An isolated polynucleotide comprising a nucleic acid sequence encoding the antibody of claim 1 or claim 2.

18. An expression vector comprising the polynucleotide of claim 17 operably linked to a cis-acting regulatory element.

19. The expression vector of claim 18 being a viral vector.

20. A cell comprising the polynucleotide of claim 17.

21. A pharmaceutical composition comprising the antibody of claim 1 or claim 2.

22. A method of treating melanoma or glioblastoma, comprising administering to a subject in need thereof a therapeutically effective amount of the antibody of claim 1 or claim 2, and wherein said melanoma or glioblastoma expresses TyrD$_{369\text{-}377}$, thereby treating the melanoma or glioblastoma.

23. A method of treating melanoma or glioblastoma, comprising administering to a subject in need thereof a therapeutically effective amount of the expression vector of claim 18, and wherein said melanoma or glioblastoma expresses TyrD$_{369\text{-}377}$, thereby treating the melanoma or glioblastoma.

24. A cell comprising the expression vector of claim 18.

25. A method of treating melanoma or glioblastoma, comprising administering to a subject in need thereof a therapeutically effective amount of a cell according to claim 20, and wherein said melanoma or glioblastoma expresses TyrD$_{369\text{-}377}$, thereby treating the melanoma or glioblastoma.

26. A method of treating melanoma or glioblastoma, comprising administering to a subject in need thereof a therapeutically effective amount of a cell according to claim 24, and wherein said melanoma or glioblastoma expresses TyrD$_{369\text{-}377}$, thereby treating the melanoma or glioblastoma.

27. An isolated polynucleotide comprising a nucleic acid sequence encoding the chimeric antigen receptor according to claim 16.

28. An expression vector comprising the polynucleotide of claim 27 operably linked to a cis-acting regulatory element.

29. The expression vector of claim 28, being a viral vector.

30. A cell comprising the polynucleotide of claim 27.

31. A cell comprising the expression vector of claim 28.

32. A method of treating melanoma or glioblastoma, comprising administering to a subject in need thereof a therapeutically effective amount of the cell according to claim 30, and wherein said melanoma or glioblastoma expresses TyrD$_{369\text{-}377}$, thereby treating the melanoma or glioblastoma.

33. A method of treating melanoma or glioblastoma, comprising administering to a subject in need thereof a therapeutically effective amount of the cell according to claim 31, and wherein said melanoma or glioblastoma expresses TyrD$_{369\text{-}377}$, thereby treating the melanoma or glioblastoma.

34. A pharmaceutical composition comprising the expression vector of claim 18.

35. A pharmaceutical composition comprising a cell of claim 20.

36. A pharmaceutical composition comprising a cell of claim 24.

37. A pharmaceutical composition comprising a cell of claim 30.

38. A pharmaceutical composition comprising a cell of claim 31.

39. The antibody of claim 2, wherein said light chain of the antibody is as set forth in SEQ ID NO: 25.

* * * * *

SEQUENCE LISTING

<160> NUMBER OF SEQ ID NOS: 39

<210> SEQ ID NO 1
<211> LENGTH: 321
<212> TYPE: DNA
<213> ORGANISM: Artificial sequence
<220> FEATURE:
<223> OTHER INFORMATION: Variable light chain

<400> SEQUENCE: 1

```
gacatccaga tgacccagtc tccatcctcc ctgtctgcat ctgtaggaga cagagtcacc    60
atcacttgca aggcgagtca ggacattcac aactatatag cttggtatca gcagaaacca   120
gggaaagccc ctaagctcct gatccactat acatccactt tgcaaccagg ggtcccatca   180
aggttcagtg gaagtggatc tgggacagat tttactttca ccatcagcag cctgcagcct   240
gaagatattg caacatatta ctgtctacag tatgataatc tctggacgtt cggtcaaggc   300
accaaggtgg aaatcaaacg g                                             321

<210> SEQ ID NO 2
<211> LENGTH: 107
<212> TYPE: PRT
<213> ORGANISM: Artificial sequence
<220> FEATURE:
<223> OTHER INFORMATION: Variable light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys Arg
            100                 105

<210> SEQ ID NO 3
<211> LENGTH: 366
<212> TYPE: DNA
<213> ORGANISM: Artificial sequence
<220> FEATURE:
<223> OTHER INFORMATION: Variable heavy chain

<400> SEQUENCE: 3
cagatcacct tgaaggagtc tggtcctacg ctggtgaaac ccacacagac cctcacgctg    60
acctgcacct tctctgggtt ctcactcagc actagtggaa tgggtgtgtc ctggatccgt   120
cagcccccag gaaaggccct ggagtggctt gcacacattt attgggatga tgataagcgc   180
tacaacccat ctctgaagag caggctcacc atcaccaagg acacctccaa aaaccaggtg   240
gtccttacaa tgaccaacat ggaccctgtg gacacagcca catattactg tgcacgaaag   300
gactacggta gtagcttcta tgctatgcac tactggggtc aaggaaccct agtcaccgtc   360
tcgagt                                                             366

<210> SEQ ID NO 4
<211> LENGTH: 122
<212> TYPE: PRT
<213> ORGANISM: Artificial sequence
<220> FEATURE:
<223> OTHER INFORMATION: Variable heavy chain

<400> SEQUENCE: 4

Gln Ile Thr Leu Lys Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
            35                  40                  45

Trp Leu Ala His Ile Tyr Trp Asp Asp Lys Arg Tyr Asn Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Lys Asp Tyr Gly Ser Ser Phe Tyr Ala Met His Tyr Trp
            100                 105                 110

Gly Gln Gly Thr Leu Val Thr Val Ser Ser
        115                 120
```

<210> SEQ ID NO 5
<211> LENGTH: 11
<212> TYPE: PRT
<213> ORGANISM: Artificial sequence
<220> FEATURE:
<223> OTHER INFORMATION: CDR1 light chain

<400> SEQUENCE: 5

```
Lys Ala Ser Gln Asp Ile His Asn Tyr Ile Ala
1               5                   10
```

<210> SEQ ID NO 6
<211> LENGTH: 7
<212> TYPE: PRT
<213> ORGANISM: Artificial sequence
<220> FEATURE:
<223> OTHER INFORMATION: CDR2 light chain

<400> SEQUENCE: 6

```
Tyr Thr Ser Thr Leu Gln Pro
1               5
```

<210> SEQ ID NO 7
<211> LENGTH: 8
<212> TYPE: PRT
<213> ORGANISM: Artificial sequence
<220> FEATURE:
<223> OTHER INFORMATION: CDR3 light chain

<400> SEQUENCE: 7

```
Leu Gln Tyr Asp Asn Leu Trp Thr
1               5
```

<210> SEQ ID NO 8
<211> LENGTH: 7
<212> TYPE: PRT
<213> ORGANISM: Artificial sequence
<220> FEATURE:
<223> OTHER INFORMATION: CDR1 Heavy chain

<400> SEQUENCE: 8

```
Thr Ser Gly Met Gly Val Ser
1               5
```

<210> SEQ ID NO 9
<211> LENGTH: 16
<212> TYPE: PRT
<213> ORGANISM: Artificial sequence
<220> FEATURE:
<223> OTHER INFORMATION: CDR2 Heavy chain

<400> SEQUENCE: 9

His Ile Tyr Trp Asp Asp Lys Arg Tyr Asn Pro Ser Leu Lys Ser
1               5                   10                  15

<210> SEQ ID NO 10
<211> LENGTH: 12
<212> TYPE: PRT
<213> ORGANISM: Artificial sequence
<220> FEATURE:
<223> OTHER INFORMATION: CDR3 Heavy chain

<400> SEQUENCE: 10

Lys Asp Tyr Gly Ser Ser Phe Tyr Ala Met His Tyr
1               5                   10

<210> SEQ ID NO 11
<211> LENGTH: 639
<212> TYPE: DNA
<213> ORGANISM: Mus musculus

<400> SEQUENCE: 11

```
gacatccaga tgacccagag ccccagcagc ctgagcgcca gcctgggcgg caaagtgacc      60
atcacatgca aggccagcca ggacatccac aactatatcg cctggtatca gcacaagccc     120
gtgaagggcc ccagactgct gatccactac accagcaccc tgcagcccgg cacccccctcc    180
agattttctg gcagcggctc cggcagagac tacagcttca gcatcagcaa cctggaaccc     240
gaggatatcg ccacctacta ctgcctgcag tacgacaacc tgtggacctt cggcggaggc     300
accaagctgg aaatcaagcg ggccgatgcc gcccctaccg tgtccatctt cccacccagc     360
tccgagcagc tgaccagcgg cggagccagc gtcgtgtgct tcctgaacaa cttctacccc     420
aaggacatca cgtgaagtg gaagatcgac ggcagcgagc ggcagaacgg cgtgctgaac     480
agctggaccg accaggacag caaggactcc acctacagca tgtccagcac actgaccctg     540
accaaggacg agtacgagag acacaactcc tatacctgcg aggccaccca caagacctcc     600
accagcccca tcgtgaagtc cttcaaccgg aacgagtgc                            639
```

<210> SEQ ID NO 12
<211> LENGTH: 213
<212> TYPE: PRT
<213> ORGANISM: Mus musculus

<400> SEQUENCE: 12

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile His Asn Tyr
            20                  25                  30

Ile Ala Trp Tyr Gln His Lys Pro Val Lys Gly Pro Arg Leu Leu Ile
        35                  40                  45

His Tyr Thr Ser Thr Leu Gln Pro Gly Thr Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 13
<211> LENGTH: 1341
<212> TYPE: DNA
<213> ORGANISM: Mus musculus

<400> SEQUENCE: 13
caagtcacac tgaaagagag cggccctggc atcctgcagc ccagccagac cctgagcctg        60
acctgcagct tcagcggctt ctccctgacc acctccggca tgggcgtgtc ctggatcaga       120
cagcctagcg gcaagggcct ggaatggctg gcccacatct actgggacga cgacaagcgg       180
tacaaccccc agctgaagtc ccggctgacc atcagcaagg acaccagccg gaaccaggtg       240
ttcctgaaga tcaccagcgt ggacgccgcc gacaccgcca cctactactg cgccagaaag       300
gactacggca gcagcttcta cgccatgcac tactggggcc agggcacctc cgtgaccgtg       360
tccagcgcca agaccacccc ccccagcgtg taccctctgg cccctggaag cgccgctcag       420
accaacagca tggtcaccct gggctgcctg gtcaagggct acttccccga gcccgtgaca       480
gtgacctgga acagcggcag cctgagcagc ggcgtgcaca cctttccagc cgtgctgcag       540
agcgacctgt acaccctgtc cagcagcgtc accgtgccca gcagcacctg gcccagcgaa       600
accgtgacct gtaacgtggc ccaccccgcc agctccacca aggtggacaa gaaaatcgtg       660
ccccgggact gcggctgcaa gccctgcatc tgcacagtgc ccgaggtgtc ctccgtgttc       720
atcttcccac ccaagcccaa ggacgtgctg acaatcaccc tgacccccaa agtgacatgc       780
gtggtggtgg acatctccaa ggatgaccca gaggtgcagt tcagttggtt cgtggacgac       840
gtggaagtgc acacagccca gacccagcct agagaggaac agttcaacag caccttcaga       900
agcgtgtccg agctgccat catgcaccag gactggctga acggcaagga attcaagtgc       960
agagtgaaca gcgccgcctt ccctgccccc atcgagaaaa ccatctctaa gaccaagggc      1020
agacccaagg cccctcaggt ctacaccatc cccccaccta agaacagat ggccaaggac      1080 aaggtgtccc tcacctgtat gatcaccgat ttcttcccag aggacatcac cgtcgagtgg      1140
cagtggaacg gccagcccgc cgagaactac aagaacaccc agccaatcat ggacaccgac      1200
ggcagctact cgtgtacag caagctgaac gtgcagaagt ccaactggga ggccggcaac      1260
accttcacct gttctgtgct gcacgagggc ctgcacaacc accaccgaa gaagtccctg      1320 tcccacagcc ccggcaagta a                                                1341

<210> SEQ ID NO 14
<211> LENGTH: 446

<212> TYPE: PRT
<213> ORGANISM: Mus musculus

<400> SEQUENCE: 14

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Ala Ala Asp Thr Ala Thr Tyr Tyr
                85                  90                  95

Cys Ala Arg Lys Asp Tyr Gly Ser Ser Phe Tyr Ala Met His Tyr Trp
                100                 105                 110

Gly Gln Gly Thr Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400
```

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 15
<211> LENGTH: 9
<212> TYPE: PRT
<213> ORGANISM: Artificial sequence
<220> FEATURE:
<223> OTHER INFORMATION: TyrD 369-377 amino acid sequence

<400> SEQUENCE: 15

Tyr Met Asp Gly Thr Met Ser Gln Val
1               5

<210> SEQ ID NO 16
<211> LENGTH: 759
<212> TYPE: PRT
<213> ORGANISM: Artificial sequence
<220> FEATURE:
<223> OTHER INFORMATION: ScFv CD3 nucleic acid sequence

<400> SEQUENCE: 16

Gly Ala Cys Ala Thr Cys Cys Ala Gly Thr Gly Ala Cys Cys Cys
1               5                   10                  15

Ala Gly Ala Gly Cys Cys Cys Ala Gly Cys Ala Gly Cys Cys Thr
            20                  25                  30

Gly Ala Gly Cys Gly Cys Cys Ala Gly Cys Gly Thr Gly Gly Gly
        35                  40                  45

Gly Ala Cys Ala Gly Ala Gly Thr Gly Ala Cys Cys Ala Thr Cys Ala
    50                  55                  60

Cys Cys Thr Gly Thr Cys Gly Gly Gly Cys Cys Ala Gly Cys Cys Ala
65                  70                  75                  80

Gly Gly Ala Cys Ala Thr Cys Cys Gly Gly Ala Ala Cys Thr Ala Cys
                85                  90                  95

Cys Thr Gly Ala Ala Cys Thr Gly Gly Thr Ala Thr Cys Ala Gly Cys
            100                 105                 110

Ala Gly Ala Ala Gly Cys Cys Cys Gly Gly Cys Ala Ala Gly Gly Cys
        115                 120                 125

Cys Cys Cys Cys Ala Ala Gly Cys Thr Gly Cys Thr Gly Ala Thr Cys
    130                 135                 140

Thr Ala Cys Thr Ala Cys Ala Cys Cys Ala Gly Cys Ala Gly Ala Cys
145                 150                 155                 160

Thr Gly Gly Ala Ala Ala Gly Cys Gly Gly Cys Gly Thr Gly Cys Cys
                165                 170                 175

Cys Ala Gly Cys Ala Gly Ala Thr Thr Cys Ala Gly Cys Gly Gly Cys
            180                 185                 190

Ala Gly Cys Gly Gly Cys Thr Cys Cys Gly Gly Cys Ala Cys Cys Gly
        195                 200                 205

Ala Cys Thr Ala Cys Ala Cys Cys Cys Thr Gly Ala Cys Cys Ala Thr
    210                 215                 220

Cys Ala Gly Cys Ala Gly Cys Cys Thr Gly Cys Ala Gly Cys Cys Cys
225                 230                 235                 240

Gly Ala Gly Gly Ala Cys Thr Thr Cys Gly Cys Cys Ala Cys Cys Thr

-continued

```
                245                 250                 255
Ala Cys Thr Ala Cys Thr Gly Cys Cys Ala Gly Cys Ala Gly Gly
            260                 265                 270
Cys Ala Ala Cys Ala Cys Cys Thr Gly Cys Cys Thr Gly Gly
            275                 280                 285
Ala Cys Cys Thr Thr Cys Gly Gly Cys Ala Ala Gly Gly Cys Ala
            290                 295                 300
Cys Cys Ala Ala Gly Gly Thr Gly Gly Ala Ala Thr Cys Ala Ala
305                 310                 315                 320
Gly Gly Gly Cys Gly Gly Ala Gly Gly Cys Gly Cys Thr Cys Thr
                325                 330                 335
Gly Gly Ala Gly Gly Cys Gly Ala Gly Gly Ala Ala Gly Cys Gly
            340                 345                 350
Gly Ala Gly Gly Cys Gly Gly Ala Gly Gly Ala Thr Cys Thr Gly
            355                 360                 365
Gly Gly Gly Ala Gly Gly Gly Gly Ala Thr Cys Thr Gly Gly Cys
            370                 375                 380
Gly Gly Ala Gly Gly Cys Thr Cys Thr Gly Ala Gly Gly Thr Gly Cys
385                 390                 395                 400
Ala Gly Cys Thr Gly Gly Thr Gly Gly Ala Ala Thr Cys Gly Gly
                405                 410                 415
Cys Gly Gly Ala Gly Gly Cys Cys Thr Gly Gly Thr Gly Cys Ala Gly
            420                 425                 430
Cys Cys Thr Gly Gly Cys Gly Gly Cys Ala Gly Cys Cys Thr Gly Ala
            435                 440                 445
Gly Ala Cys Thr Gly Thr Cys Thr Thr Gly Thr Gly Cys Cys Gly Cys
            450                 455                 460
Cys Ala Gly Cys Gly Gly Cys Thr Ala Cys Ala Gly Cys Thr Thr Cys
465                 470                 475                 480
Ala Cys Cys Gly Gly Cys Thr Ala Cys Ala Cys Cys Ala Thr Gly Ala
                485                 490                 495
Ala Cys Thr Gly Gly Gly Thr Cys Cys Gly Ala Cys Ala Ala Gly Cys
            500                 505                 510
Cys Cys Cys Thr Gly Gly Cys Ala Ala Gly Gly Cys Cys Thr Gly
            515                 520                 525
Gly Ala Ala Thr Gly Gly Gly Thr Gly Gly Cys Cys Cys Thr Gly Ala
            530                 535                 540
Thr Cys Ala Ala Cys Cys Cys Thr Ala Cys Ala Ala Gly Gly Gly
545                 550                 555                 560
Cys Gly Thr Gly Thr Cys Cys Ala Cys Thr Ala Cys Ala Ala Cys
                565                 570                 575
Cys Ala Gly Ala Ala Gly Thr Thr Cys Ala Ala Gly Gly Ala Cys Cys
            580                 585                 590
Gly Gly Thr Thr Cys Ala Cys Cys Ala Thr Cys Ala Gly Cys Gly Thr
            595                 600                 605
Gly Gly Ala Cys Ala Ala Gly Ala Gly Cys Ala Ala Gly Ala Ala Cys
            610                 615                 620
Ala Cys Cys Gly Cys Cys Thr Ala Cys Thr Gly Cys Ala Gly Ala
625                 630                 635                 640
Thr Gly Ala Ala Cys Ala Gly Cys Cys Thr Gly Ala Gly Ala Gly Cys
                645                 650                 655
Cys Gly Ala Gly Gly Ala Cys Ala Cys Cys Gly Cys Cys Gly Thr Gly
            660                 665                 670
```

```
Thr Ala Cys Thr Ala Cys Thr Gly Cys Gly Cys Cys Ala Gly Ala Ala
            675                 680                 685

Gly Cys Gly Gly Cys Thr Ala Cys Thr Ala Cys Gly Cys Gly Cys Ala
        690                 695                 700

Cys Ala Gly Cys Gly Ala Cys Thr Gly Gly Thr Ala Cys Thr Thr Cys
705                 710                 715                 720

Gly Ala Cys Gly Thr Gly Thr Gly Gly Gly Cys Cys Ala Gly Gly
                725                 730                 735

Gly Ala Ala Cys Cys Cys Thr Gly Gly Thr Cys Ala Cys Cys Gly Thr
            740                 745                 750

Gly Thr Cys Thr Ala Gly Cys
            755
```

<210> SEQ ID NO 17
<211> LENGTH: 253
<212> TYPE: PRT
<213> ORGANISM: Artificial sequence
<220> FEATURE:
<223> OTHER INFORMATION: ScFv CD3 amino acid sequence

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser
                245                 250
```

<210> SEQ ID NO 18

<211> LENGTH: 639
<212> TYPE: DNA
<213> ORGANISM: Artificial sequence
<220> FEATURE:
<223> OTHER INFORMATION: Light chain D11 in BS nucleic acid sequence

<400> SEQUENCE: 18

```
gatattcaga tgacccagtc tcctagctct ctgtctgcca gcctcggcgg caaagtgaca      60
atcacatgca aggcctctca ggatatccac aactatatcg cctggtatca acacaaaccc     120
gtgaagggac ccagactgct gattcactat acaagcaccc tgcagccagg cacacctagc     180
agattcagcg gaagcggcag cggaagagac tactccttca gcatcagcaa cctggaacca     240
gaggacattg ccacatatta ctgcctgcag tacgacaacc tgtggacctt cggaggcgga     300
acaaagctcg agatcaagag aacagtggcc gctcctagcg tgttcatctt cccaccaagc     360
gacgagcagc tgaagtctgg cacagcctct gtcgtgtgcc tgctgaacaa cttctacccc     420
agagaagcca aggtgcagtg gaaggtggac aatgccctgc agagcggcaa tagccaagag     480
agcgtgaccg agcaggacag caaggatagc acctatagcc tgagcagcac actgaccctg     540
agcaaggccg actacgagaa gcacaaagtg tacgcctgcg aagtgacaca ccagggactg     600
agcagccctg tgaccaagag cttcaacaga ggcgagtgc                            639
```

<210> SEQ ID NO 19
<211> LENGTH: 213
<212> TYPE: PRT
<213> ORGANISM: Artificial sequence
<220> FEATURE:
<223> OTHER INFORMATION: Light chain D11 in BS amino acid sequence

<400> SEQUENCE: 19

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile His Asn Tyr
            20                  25                  30

Ile Ala Trp Tyr Gln His Lys Pro Val Lys Gly Pro Arg Leu Leu Ile
        35                  40                  45

His Tyr Thr Ser Thr Leu Gln Pro Gly Thr Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 20
<211> LENGTH: 675
<212> TYPE: DNA
<213> ORGANISM: Artificial sequence
<220> FEATURE:
<223> OTHER INFORMATION: VHCH1 in BS nucleic acis sequence

<400> SEQUENCE: 20

| | | |
|---|---|---|
| cagatcaccc tgaaagaatc tggccctaca ctggtcaagc ccacacagac cctgacactg | 60 |
| acctgcacct ttagcggctt tagcctgagc acaagcggca tgggagtgtc ctggattaga | 120 |
| cagcctcctg gaaaggccct cgaatggctg gcccacatct actgggacga cgacaagaga | 180 |
| tacaacccca gcctgaagtc ccggctgaca atcaccaagg acaccagcaa gaaccaggtg | 240 |
| gtgctgacca tgaccaacat ggaccctgtg acaccgcta cctactattg cgcccggaag | 300 |
| gattacggca gcagcttcta cgccatgcac tactggggac agggcacact cgtgacagtg | 360 |
| tctagcgcct ctacaaaggg ccctagcgtt ttcccactgg ctcctagcag caagtctaca | 420 |
| agcggaggaa cagccgctct gggctgcctg gtcaaggatt actttcctga gcctgtgacc | 480 |
| gtgtcttgga actctggtgc tctgacctcc ggcgtgcaca catttccagc cgtgctgcag | 540 |
| tctagcggcc tgtactctct gagcagcgtt gtgacagtgc caagctctag cctgggcacc | 600 |
| cagacctaca tctgcaacgt gaaccacaag cctagcaaca ccaaggtcga caagaaggtg | 660 |
| gaacccaaga gctgc | 675 |

<210> SEQ ID NO 21
<211> LENGTH: 225
<212> TYPE: PRT
<213> ORGANISM: Artificial sequence
<220> FEATURE:
<223> OTHER INFORMATION: VHCH1 in BS amino acid sequence

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Asp Tyr Gly Ser Ser Phe Tyr Ala Met His Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 22
<211> LENGTH: 33
<212> TYPE: DNA
<213> ORGANISM: Artificial sequence
<220> FEATURE:
<223> OTHER INFORMATION: CDR1 light chain nucleic acid sequence

<400> SEQUENCE: 22
aaggcgagtc aggacattca aactatata gct                              33

<210> SEQ ID NO 23
<211> LENGTH: 21
<212> TYPE: DNA
<213> ORGANISM: Artificial sequence
<220> FEATURE:
<223> OTHER INFORMATION: CDR2 light chain nucleic acid sequence

<400> SEQUENCE: 23
tatacatcca ctttgcaacc a                                          21

<210> SEQ ID NO 24
<211> LENGTH: 639
<212> TYPE: DNA
<213> ORGANISM: Artificial sequence
<220> FEATURE:
<223> OTHER INFORMATION: hD11-5 Full length light chain nucleic acid
      sequence

<400> SEQUENCE: 24
gacatccaga tgacccagtc tccatcctcc ctgtctgcat ctgtaggaga cagagtcacc    60
atcacttgca aggcgagtca ggacattcac aactatatag cttggtatca gcagaaacca   120
gggaaagccc ctaagctcct gatccactat acatccactt tgcaaccagg gtcccatca    180 aggttcagtg gaagtggatc tgggacagat tttactttca ccatcagcag cctgcagcct   240
gaagatattg caacatatta ctgtctacag tatgataatc tctggacgtt cggtcaaggc   300
accaaggtgg aaatcaaacg gaccgtggcc gcacctagtg tgttcatctt ccctccctcc   360
gacgagcagc tgaagtctgg caccgcctcc gtggtctgcc tgctgaacaa cttctaccct   420
cgggaggcca aggtgcagtg gaaggtggac aacgccctgc agtccggcaa ctcccaggaa   480
tccgtcaccg agcaggactc caaggactct acctactccc tgtcctccac cctgaccctg   540
tccaaggccg actacgagaa gcacaaggta cgcctgcg aggtcaccca ccagggcctg    600
tcctctcccg tcaccaagtc cttcaaccgg ggcgagtgc                          639

<210> SEQ ID NO 25
<211> LENGTH: 213
<212> TYPE: PRT
<213> ORGANISM: Artificial sequence
<220> FEATURE:
<223> OTHER INFORMATION: hD11-5 Full length light chain amino acid
      sequence
```

<400> SEQUENCE: 25

```
Asp Ile Gln Met Thr Gln Ser Pro Ser Leu Ser Ala Ser Val Gly
1               5                   10                  15
Asp Arg Val Thr Ile Thr Cys Lys Ala Ser Gln Asp Ile His Asn Tyr
            20                  25                  30
Ile Ala Trp Tyr Gln Gln Lys Pro Gly Lys Ala Pro Lys Leu Leu Ile
        35                  40                  45
His Tyr Thr Ser Thr Leu Gln Pro Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Leu Gln Tyr Asp Asn Leu Trp Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 26
<211> LENGTH: 1353
<212> TYPE: DNA
<213> ORGANISM: Artificial sequence
<220> FEATURE:
<223> OTHER INFORMATION: hD11-5 Full length heavy chain nucleic acid sequence

<400> SEQUENCE: 26

```
cagatcacct tgaaggagtc tggtcctacg ctggtgaaac ccacacagac cctcacgctg     60
acctgcacct tctctgggtt ctcactcagc actagtggaa tgggtgtgtc ctggatccgt    120
cagcccccag gaaaggccct ggagtggctt gcacacattt attgggatga tgataagcgc    180
tacaacccat ctctgaagag caggctcacc atcaccaagg acacctccaa aaaccaggtg    240
gtccttacaa tgaccaacat ggaccctgtg acacagcca catattactg tgcacgaaag    300
gactacggta gtagcttcta tgctatgcac tactggggtc aaggaaccct agtcaccgtc    360
tcgagtgcct ctaccaaggg cccttccgtg ttccctctgg ccccagctc gaagtccacc     420
tccggcggca ccgccgctct gggctgcctg gtcaaggact acttccctga gcctgtgaca    480
gtgtcctgga actctggcgc tctgacctct ggcgtgcata ccttccctgc cgtgctgcag    540
tcctccggcc tgtactccct gtcctctgtg gtcacagtgc cttcctcctc cctgggcacc    600
cagacctaca tctgcaacgt gaaccacaag ccttccaaca ccaaggtgga caagaaggtg    660
gagcctaagt cctgcgacaa gacccacacc tgtcctccct gccctgctcc tgagctgctg    720
```

| | | |
|---|---|---|
| ggcggaccct ccgtgttcct gttccctcct aagcctaagg acaccctgat gatctcccgg | 780 | |
| accccctgagg tcacctgtgt ggtggtggat gtgtcccacg aggatcctga ggtcaagttc | 840 | |
| aattggtacg tggacggcgt ggaggtgcac aacgccaaga caaagccacg cgaggaacag | 900 | |
| tacaactcca cctaccgggt ggtgtccgtg ctgaccgtgc tgcaccagga ctggctgaac | 960 | |
| ggcaaagagt acaagtgcaa ggtctccaac aaggccctgc ctgccccat cgagaaaacc | 1020 | |
| atctccaagg ccaagggaca gcctcgcgag cctcaggtgt acaccctgcc tccctctcgg | 1080 | |
| gatgaactga ccaagaatca ggtgtccctg acatgtctgg tcaagggctt ctacccttcc | 1140 | |
| gatatcgccg tggagtggga gtccaacggc cagcctgaga caactacaa gaccacccct | 1200 | |
| cctgtgctgg actccgacgg ctcttttcttc ctgtactcca agctgaccgt ggacaagtcc | 1260 | |
| cggtggcagc agggcaacgt gttcctcctgc tccgtgatgc acgaggccct gcacaaccac | 1320 | |
| tacacccaga gtctctgtc cctctctccc ggc | 1353 | |

<210> SEQ ID NO 27
<211> LENGTH: 451
<212> TYPE: PRT
<213> ORGANISM: Artificial sequence
<220> FEATURE:
<223> OTHER INFORMATION: hD11-5 Full length heavy chain amino acid
      sequence

<400> SEQUENCE: 27

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Asp Tyr Gly Ser Ser Phe Tyr Ala Met His Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu

```
              245                 250                 255
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly
    450

<210> SEQ ID NO 28
<211> LENGTH: 24
<212> TYPE: DNA
<213> ORGANISM: Artificial sequence
<220> FEATURE:
<223> OTHER INFORMATION: CDR3 light chain nucleic acid sequence

<400> SEQUENCE: 28
ctacagtatg ataatctctg gacg                                              24

<210> SEQ ID NO 29
<211> LENGTH: 21
<212> TYPE: DNA
<213> ORGANISM: Artificial sequence
<220> FEATURE:
<223> OTHER INFORMATION: CDR1 Heavy chain nucleic acid sequence

<400> SEQUENCE: 29
actagtggaa tgggtgtgtc c                                                 21

<210> SEQ ID NO 30
<211> LENGTH: 48
<212> TYPE: DNA
<213> ORGANISM: Artificial sequence
<220> FEATURE:
<223> OTHER INFORMATION: CDR2 Heavy chain nucleic acid sequence

<400> SEQUENCE: 30
cacatttatt gggatgatga taagcgctac aacccatctc tgaagagc                    48

<210> SEQ ID NO 31
```

```
<211> LENGTH: 36
<212> TYPE: DNA
<213> ORGANISM: Artificial sequence
<220> FEATURE:
<223> OTHER INFORMATION: CDR3 Heavy chain nucleic acid sequence

<400> SEQUENCE: 31
aaggactacg gtagtagctt ctatgctatg cactac                              36

<210> SEQ ID NO 32
<211> LENGTH: 15
<212> TYPE: DNA
<213> ORGANISM: Artificial sequence
<220> FEATURE:
<223> OTHER INFORMATION: Connector between anti CD3 to D11 VL  nucleic
      acid sequence

<400> SEQUENCE: 32
ggcggtggcg gaagc                                                     15

<210> SEQ ID NO 33
<211> LENGTH: 5
<212> TYPE: PRT
<213> ORGANISM: Artificial sequence
<220> FEATURE:
<223> OTHER INFORMATION: Connector between anti CD3 to D11 VL  amino
      acid sequence

<400> SEQUENCE: 33

Gly Gly Gly Gly Ser
1               5

<210> SEQ ID NO 34
<211> LENGTH: 57
<212> TYPE: DNA
<213> ORGANISM: Artificial sequence
<220> FEATURE:
<223> OTHER INFORMATION: Mouse IgH signal sequence - leader sequence for
      expression in pCDNA3.4

<400> SEQUENCE: 34
atgggatgga gctgtatcat cctcttcttg gtagcaacag ctacaggtgt acactcc       57

<210> SEQ ID NO 35
<211> LENGTH: 19
<212> TYPE: PRT
<213> ORGANISM: Artificial sequence
<220> FEATURE:
<223> OTHER INFORMATION: Mouse IgH signal sequence - leader sequence for
      expression in pCDNA3.4

<400> SEQUENCE: 35

Met Gly Trp Ser Cys Ile Ile Leu Phe Leu Val Ala Thr Ala Thr Gly
1               5                   10                  15
Val His Ser

<210> SEQ ID NO 36
<211> LENGTH: 60
<212> TYPE: DNA
<213> ORGANISM: Artificial sequence
<220> FEATURE:
<223> OTHER INFORMATION: Leader sequence for expression in pCI Light
      chain

<400> SEQUENCE: 36
atggagacag acacactcct gctatgggta ctgctgctct gggtcccggg atccactggt    60
```

```
<210> SEQ ID NO 37
<211> LENGTH: 20
<212> TYPE: PRT
<213> ORGANISM: Artificial sequence
<220> FEATURE:
<223> OTHER INFORMATION: Leader sequence for expression in pCI Light
      chain

<400> SEQUENCE: 37

Met Glu Thr Asp Thr Leu Leu Leu Trp Val Leu Leu Leu Trp Val Pro
1               5                  10                  15

Gly Ser Thr Gly
            20

<210> SEQ ID NO 38
<211> LENGTH: 57
<212> TYPE: DNA
<213> ORGANISM: Artificial sequence
<220> FEATURE:
<223> OTHER INFORMATION: Leader sequence for expression in pCI Heavy
      chain

<400> SEQUENCE: 38
atggaatggt cctgggtgtt cctgttcttc ctgtccgtga ccaccggtgt gcactcc     57

<210> SEQ ID NO 39
<211> LENGTH: 19
<212> TYPE: PRT
<213> ORGANISM: Artificial sequence
<220> FEATURE:
<223> OTHER INFORMATION: Leader sequence for expression in pCI Heavy
      chain

<400> SEQUENCE: 39

Met Glu Trp Ser Trp Val Phe Leu Phe Phe Leu Ser Val Thr Thr Gly
1               5                  10                  15

Val His Ser
```